(12) United States Patent
Stanley

(10) Patent No.: US 6,797,234 B2
(45) Date of Patent: Sep. 28, 2004

(54) REVERSE FLOW STERILIZING METHOD

(75) Inventor: Patricia M. Stanley, Minneapolis, MN (US)

(73) Assignee: Minntech Corporation, Minneapolis, MN (US)

( * ) Notice: Subject to any disclaimer, the term of this patent is extended or adjusted under 35 U.S.C. 154(b) by 507 days.

(21) Appl. No.: 09/867,047

(22) Filed: May 29, 2001

(65) Prior Publication Data

US 2004/0156744 A9 Aug. 12, 2004

Related U.S. Application Data

(62) Division of application No. 09/409,101, filed on Sep. 30, 1999, now Pat. No. 6,286,527.
(60) Provisional application No. 60/117,401, filed on Jan. 27, 1999, provisional application No. 60/102,663, filed on Oct. 1, 1998, and provisional application No. 60/102,664, filed on Oct. 1, 1998.

(51) Int. Cl.[7] ............................................... A61L 2/00
(52) U.S. Cl. .................. 422/28; 134/22.12; 134/166 R; 134/169; 422/1; 422/34; 422/292
(58) Field of Search ............................... 422/28, 1, 34, 422/292; 600/133, 139; 134/22.1, 22.18, 22.11, 22.12, 166 R, 169

(56) References Cited

U.S. PATENT DOCUMENTS

| 3,893,843 A | 7/1975 | Fry et al. |
| 4,067,691 A | 1/1978 | McGrady et al. |
| 4,261,950 A | 4/1981 | Bainbridge et al. |
| 4,281,674 A | 8/1981 | Tanaka et al. |
| 4,299,244 A | 11/1981 | Hirai |
| 4,354,514 A | 10/1982 | Sundheimer et al. |
| 4,517,081 A | 5/1985 | Amiot et al. |
| 4,526,623 A | 7/1985 | Ishii et al. |
| 4,579,597 A | 4/1986 | Sasa et al. |

(List continued on next page.)

FOREIGN PATENT DOCUMENTS

| GB | 2 248 188 A | 4/1992 |
| WO | WO 97/17665 | 5/1997 |

OTHER PUBLICATIONS

UNITROL (Infection Control Division of Minntech Corporation); AERO PLUS Automatic Endoscope Reprocessor, 1984 Brochure.
UNITROL (Infection Control Division of Minntech Corporation); AERO Automatic Endoscope Reprocessor, 1994 Brochure.

Primary Examiner—Krisanne Jastrzab
(74) Attorney, Agent, or Firm—Suzanne J. London

(57) ABSTRACT

A device and method for cleaning and sterilizing tubular structures particularly, long, narrow tubular structures such as lumens of a medical device such as an endoscope by reversing the flow of fluid in interconnected tubular structures. The device comprises a first and second valve in fluid communication with a first and second tubular structure. The valves selectively switch between a first and second position causing a first and second flow path within the tubular structures, at least a part of the second flow path opposite the first flow path.

17 Claims, 36 Drawing Sheets

U.S. PATENT DOCUMENTS

| | | | |
|---|---|---|---|
| 4,644,478 A | 2/1987 | Stephens et al. | |
| 4,721,123 A | 1/1988 | Cosentino et al. | |
| 4,763,678 A | 8/1988 | Ott | |
| 4,892,706 A | 1/1990 | Kralovic et al. | |
| 4,943,414 A | 7/1990 | Jacobs et al. | |
| 5,217,698 A | 6/1993 | Siegel et al. | |
| 5,225,160 A | 7/1993 | Sanford et al. | |
| 5,279,799 A | 1/1994 | Moser | |
| 5,288,467 A | 2/1994 | Biermaier | |
| 5,310,524 A | 5/1994 | Campbell et al. | |
| 5,399,314 A | 3/1995 | Samuel et al. | |
| 5,408,991 A | * 4/1995 | Iida et al. | 128/4 |
| 5,425,815 A | 6/1995 | Parker et al. | |
| 5,443,801 A | 8/1995 | Langford | |
| 5,492,672 A | 2/1996 | Childers et al. | |
| 5,494,637 A | 2/1996 | Barlow | |
| 5,529,750 A | 6/1996 | Kochte | |
| 5,552,115 A | 9/1996 | Malchesky | |
| 5,556,607 A | 9/1996 | Childers et al. | |
| 5,558,841 A | 9/1996 | Nakagawa et al. | |
| 5,711,921 A | 1/1998 | Langford | |
| 5,733,503 A | 3/1998 | Kowatsch et al. | |
| 5,746,988 A | 5/1998 | Hall | |
| 5,753,195 A | 5/1998 | Langford et al. | |
| 5,792,435 A | 8/1998 | Mueller et al. | |
| 5,795,404 A | 8/1998 | Murphy et al. | |
| 5,858,305 A | 1/1999 | Malchesky | |
| 6,286,527 B1 | 9/2001 | Stanley | |
| 6,439,246 B2 | 8/2002 | Stanley | |

* cited by examiner

Fig.9

| FIG. 9A | FIG. 9B | FIG. 9C | FIG. 9D |
|---------|---------|---------|---------|
| FIG. 9E | FIG. 9F | FIG. 9G | FIG. 9H |

Fig. 10

| FIG. 10A | FIG. 10B | FIG. 10C | FIG. 10D |
|----------|----------|----------|----------|
| FIG. 10E | FIG. 10F | FIG. 10G | FIG. 10H |

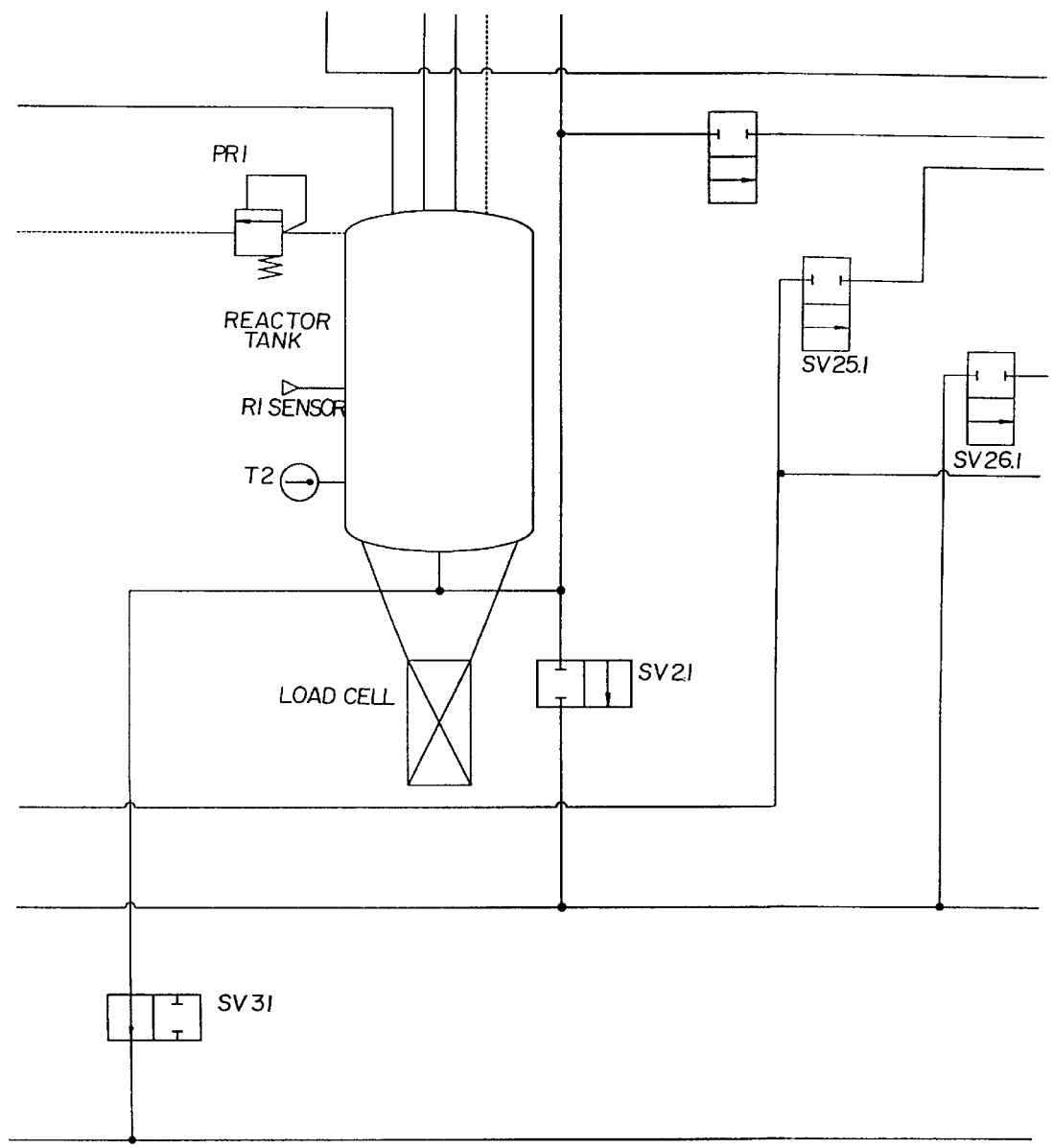

REVERSE FLOW STERILIZING METHOD

This application is a division of U.S. application Ser. No. 09/409,101, filed Sep. 30, 1999, now U.S. Pat. No. 6,286, 527, which claims the benefit of provisional Application No. 60/102,663, filed Oct. 1, 1998, provisional Application No. 60/102,664, filed Oct. 1, 1998 and provisional Application No. 60/117,401, filed Jan. 27, 1999.

BACKGROUND OF THE INVENTION

1. Field of the Invention

This invention relates generally to the field of sterilizing and cleaning tubular structures including long, narrow, tubular structures. In particular, it relates to a device and method for cleaning and sterilizing medical devices with lumens.

2. Description of the Related Art

Many tubular structures, in particular flexible fiber endoscopes, define long tortuous lumens. These lumens are typically from about 1 m to about 4 m long with inside diameters from about 0.5 mm to about 6 mm and frequently contain crevices, bends, connections, restrictions, and irregularities. These instruments are frequently used in diagnostic medicine, requiring penetration into the human body or other contact with the human bloodstream. It is, therefore, desirable that they are cleaned, rinsed, sterilized, disinfected, or otherwise treated with fluid chemical disinfectants or sterilants to prevent the cross contamination and transmission of pathogenic organisms from patient to patient. In order for fluid chemical sterilization to be effective, the chemical must reach all internal and external surfaces. Efficaciousness, therefore, is severely limited by the inherent irregularities present in the long, narrow, lumens of flexible fiber endoscopes making effective cleaning and sterilization difficult.

Consistently and quickly cleaning, disinfecting, and sterilizing medical devices is an important part of providing quality healthcare. Failure to consistently clean and sterilize medical instruments leads to unwanted transmission of bacteria, viruses, and other organisms to and from patients. Improper handling of medical instruments allows unwanted organisms access inside the body where they may cause infection and disease.

Although the terms "sterilization" and "disinfection" are sometimes used imprecisely, the medical industry and regulatory agencies have more precisely defined the following terms including subdividing disinfection into high, intermediate, and low level disinfection.

Sterilization is generally defined as the destruction or elimination of all microbial life forms. Operationally, a sterilizing process is one that destroys all microbes on a device that has been contaminated with $10^6$ bacterial endospores.

High level disinfection is generally defined as the destruction or elimination of all microbial life forms except microbial spores. High level disinfectants however, must show a capability of destroying bacterial spores over an extended period of time.

Intermediate disinfection is generally defined as the destruction of all microbial life forms except bacterial spores and some viruses. However, intermediate disinfection requires the destruction or elimination of Mycobacterium tuberculosis var. bovis, which is a relatively difficult bacterium to destroy.

Low level disinfection is generally defined as the destruction of vegetative forms of bacteria (such as salmonellae and staphylococci), most fungi, medium sized or lipid containing viruses (such as Herpes simplex virus, hepatitis B virus, and HIV), but not bacterial endospores, mycobacteria, or small or non-lipid viruses (such as poliovirus and rhinovirus).

The level of disinfection or sterilization desired for a particular piece of equipment generally depends on the degree of exposure the equipment poses to the patient. For example, sterilization is generally necessary for equipment that is introduced directly into the human body, either in contact with the blood stream, or in contact with normally sterile areas of the body. High level disinfection is generally required for equipment that contacts mucus membranes, but does not penetrate bodily surfaces. Low and intermediate disinfection is generally required for equipment that contacts unbroken skin.

Endoscopes, which are used to probe internal passages of the body, are an exception to the general rule of sterilizing equipment that is introduced directly into the human body. Ideally, all endoscopes should be cleaned and sterilized between uses. However, due to their delicate optical equipment, endoscopes remain an exception to the sterilization rule. The delicate optical equipment and lenses in these devices do not allow conventional methods of sterilization such as autoclaving, ethylene oxide gassing, or soaking for several hours in liquid sterilants. Autoclaving requires high temperatures for sterilization, which damages the optical lenses of the endoscopes. Ethylene oxide gas equipment is expensive and requires several hours to complete the sterilization and degassing process. Repeated soaking in liquid sterilants may also damage some endoscopes. In addition, the high cost of these specialized pieces of equipment demands efficient utilization of the instruments, requiring use of the same endoscope on as many patients in as little time as feasible. Therefore, soaking in liquid sterilants or sterilization by ethylene oxide gas is not economically feasible because of the long time period required. The demand for rapid reuse results in pressure to shorten or eliminate cleaning, disinfection, and sterilization practices. As a compromise to all of these considerations, high level disinfection for endoscopes is conventionally accepted in lieu of sterilization.

Although high level disinfection has been conventionally acceptable, it does not provide the level of safety of sterilization. The conventional rationale for accepting the reduced level of safety is that endoscopes contact mucus membrane and do not provide access to the blood stream. However, endoscopes are routinely used to find lesions in mucus membrane areas that may provide access to the blood stream. In addition, many endoscopes provide biopsy forceps that are miniature scalpels used to cut biopsy samples from the mucus membrane tissue. These common practices provide access to the bloodstream and a potential pathway for unwanted organisms to access all parts of the body. In addition to providing a direct path to the bloodstream, many endoscopes such as duodenoscopes are used in normally sterile parts of the body. Introducing contaminated equipment into these areas has been shown to cause infection.

The lumens of medical devices have conventionally been difficult to clean, disinfect, and sterilize. Some larger lumens may be cleaned with brushes. However, lumens that are too small for brushes are generally limited to cleaning by flushing with fluids such as water or air. As noted previously, the lumens also contain crevices, bends, connections, restrictions, and irregularities that restrict flow and hold residual material making cleaning difficult. Before a piece of equipment is disinfected or sterilized, it is preferably first cleaned. Failure to completely clean residual material from the equipment potentially leaves microorganisms within and beneath the residual material not easily accessible to the disinfectant or sterilant.

Some conventional devices have used special attachments or caps to direct flow into different passages of endoscopes. However, these attachments create additional attachment points. The unexposed surfaces between the attachment and the medical device may not receive complete cleaning or sterilization.

Typically, conventional devices and methods of cleaning have used uni-directional flow to clean long narrow devices with lumens. It is believed that irregularities and restrictions in the passages create air pockets or sheltered areas along the passages. For example, as the fluid flows around corners, the fluid tends to flow to the outside of the corner, leaving an air pocket or undisturbed liquid or material on the inside edge. Fluid flow is also reduced on the downstream side of any restriction.

Some devices, such as those disclosed in Ishii U.S. Pat. No. 4,526,623, use suction from a syringe to draw residual fluid in the lumens or to draw fluid from an additional fluid container. However, the use of suction may collapse lumens, introduce additional air pockets in the lumen, and create the need for additional attachments. Suction may also require the use of check valves to properly control the removal of fluid and reduce the amount of air introduced into the medical device. Check valves may also reduce or eliminate complete removal of the fluid. Cleaning by suction only removes liquid from multiple lumens until one lumen contains air. Once a single lumen contains air, only air is drawn through the device because air flows more easily than liquid. The relative differences in the size of the lumens would also cause certain lumens to drain more quickly, leaving liquid in the remaining lumens. Lastly, the syringe method and device of Ishii is not easily automated.

Sterilization methods have also included immersion or soaking of medical devices in liquid sterilant. Sterilization by soaking typically requires several hours and air bubbles may become trapped inside the lumens, causing inconsistent results.

A new and useful device and method is needed that overcomes the problems associated with conventional methods of cleaning and sterilizing tubular structures, including long, narrow, tubular structures, particularly medical devices with lumens, by providing a device and method that provides a reverse flow through the tubular structures.

SUMMARY OF THE INVENTION

It is an object of the reverse flow cleaning and sterilizing device and method in accordance with the present invention to solve the problems outlined above that have heretofore inhibited the successful cleaning and sterilization of tubular structures, in particular, long, narrow, tubular structures.

More particularly, the apparatus and method of the reverse flow cleaning and sterilizing device in accordance with the present invention provides for the cleaning and sterilization of medical devices with lumens, particularly endoscope lumens.

The unique sterilization and cleaning device in accordance with the present invention broadly includes a first valve and a second valve. The first and second valves are each in fluid communication with a fluid supply at a positive pressure. The first valve is in fluid communication with a first tubular structure having a proximal end and a distal end with the first valve in fluid communication with the proximal end. The second valve is in fluid communication with a second tubular structure having a proximal and a distal end with the second valve in fluid communication with the proximal end. The first tubular structure is in fluid communication with the second tubular structure. The first and second valves selectively switch between a first position and a second position. The first position causes a first fluid flow path and the second position causes a second fluid flow path. At least part of the second fluid flow path is opposite the first fluid flow path. In the first position the first valve is open to the fluid supply and the second valve is closed to the fluid supply. In the second position the second valve is open to the fluid supply and the first valve is closed to the fluid supply.

The device may also provide that either both fluid flow paths start at one end of a medical device or one fluid flow path may start in a control head or center of the medical device.

The device may also provide that the distal end of at least one of the tubular structures is open to a drain at about atmospheric pressure.

The device may also provide that in the first position the second valve is open to a drain line and in the second position the first valve is open to a drain line.

The device may also provide that the fluid supply has a flow volume from about 100 ml/min to about 1400 ml/min and a flow velocity from about 50 cm/sec to about 500 cm/sec and a pressure below about 20 psi for about 1 minute to about 20 minutes.

The device may also provide a third and a fourth valve, a third and a fourth tubular structure, and a third and a fourth position.

The device may also be used in an automatic reprocessing device so that a central processor controls positioning of the valves.

The apparatus and method in accordance with the present invention provides both a method of sterilization of tubular structures and a method of cleaning the lumens of a medical device.

The sterilization method broadly includes the sterilization of the interior of a tubular structure comprising: a) providing a tubular structure, b) providing a sterilizing fluid c) causing the sterilizing fluid to flow at a positive pressure through the tubular structure in a first fluid flow path, and d) causing the sterilizing fluid to reverse flow at a positive pressure through the tubular structure in a second fluid flow path, so that at least part of the second fluid flow path is opposite the first fluid flow path.

The sterilization method may also include providing the sterilizing fluid at a temperature from about 20 degrees C. to about 50 degrees C. and from about 1 minute to about 20 minutes.

The sterilization method may also include providing a tubular structure having a diameter equal to or less than about 6 mm and the flowing and the reverse flowing have a flow velocity from about 50 cm/second to about 500 cm/second, a flow volume from about 100 ml/min to about 1400 ml/min, and a pressure below about 20 psi.

The sterilization method may also include starting the first fluid flow path and starting the second fluid flow path in one end of a medical device.

The device may also provide that one fluid flow path may start in a control head or other attachment point of the medical device.

The sterilization method may also include providing the device of the present invention.

The sterilization method may also include controlling the flowing and the reverse flowing by a central processor.

The present invention may also include a method of cleaning a medical device with lumens. The cleaning method broadly includes a method of cleaning the lumens of a medical device including a) providing a medical device with a first lumen and a second lumen, each lumen having a proximal end and a distal end, the first lumen in fluid communication with the second lumen, and the second end of at least one of the lumens open to a drain at about atmospheric pressure; b) providing a cleaning fluid; c) causing the cleaning fluid to flow at a positive pressure through the lumens in a first fluid flow path starting at the proximal end of the first lumen; and d) causing the cleaning fluid to reverse flow at a positive pressure through the lumens in a second fluid flow path starting at the proximal end of the second lumen, such that at least part of the second fluid flow path is opposite the first fluid flow path.

The cleaning method may also include providing a medical device with the first end of each lumen located in the same end of the medical device.

The cleaning method may also provide that either both fluid flow paths start at one end of a medical device or one fluid flow path may start in a control head or other attachment point of the medical device.

The cleaning method may also include draining the first fluid flow path through the proximal end of the second lumen and draining the second fluid flow path through the proximal end of the first lumen.

The cleaning method may also include providing the flowing and the reverse flowing at a flow velocity of from about 50 cm/sec to about 500 cm/sec, a flow volume from about 100 ml/min to about 1400 ml/min, and a pressure below about 20 psi.

The cleaning method may also include providing the device of the present invention.

The cleaning method may also provide controlling the flowing and the reverse flowing by a central processor.

One advantage of the present invention is improved sterilization. The present invention provides better application of the fluid to all parts of the interior of tubular structures. Improved application of the fluid to the interior of the tubular structure results in faster and more consistent sterilization.

Another advantage is that air pockets are consistently removed. The present invention improves sterilization and cleaning by providing better application of fluid by consistently removing air pockets from the interior of the tubular structures. Flowing and reverse flowing at a positive pressure provides consistent removal of air pockets. Soaking or holding fluid in the tubular structures does not consistently remove air pockets resulting in inconsistent cleaning and sterilization.

Another advantage is that the fluid obtains improved access to cracks, crevices, and restrictions. Flowing and reverse flowing at a positive pressure forces fluid into cracks, crevices, and restrictions from more than one direction. Flowing from one direction or flowing at a negative pressure does not force fluid into the cracks and crevices, especially downstream of a restriction, causing inconsistent sterilization and cleaning.

Another advantage is that residual liquids and materials remaining in the lumens are more adequately displaced with fluid. Liquid, such as left over rinse water may not be completely displaced using an uni-directional flow pattern. As a result, the chemicals (active ingredients) in the fluid must diffuse into the rinse water before sterilization may occur. The present invention provides better displacement of residual materials and liquids providing faster and more consistent sterilization and cleaning.

Another advantage is that soaking is not required. The present invention is not limited by the use of large volumes of sterilizing fluid needed to immerse the entire tubular structure, saving sterilization fluid.

Another advantage is that sterilization can be accomplished more quickly. Long soaking times of hours required for immersion sterilization may be reduced to about minutes for the present invention. Quicker sterilization results in better utilization of medical equipment.

Another advantage is that sterilization can be accomplished more consistently. Flowing sterilizing fluid from more than one direction and forcing the sterilizing fluid into cracks and crevices with positive pressure reaches the interior surfaces of tubular structures more consistently. More consistent application of the sterilizing fluid to the interior surfaces provides more consistent sterilization.

Another advantage is that the present invention can be attached to the supply ports of the endoscope. The present invention may be attached to one end of a medical device such as an endoscope without any attachments to the distal end or insertion section of the medical device. Other methods using suction pressure require the attachment of a fluid source in addition to the suction source requiring additional attachments. A device that connects to one end of the medical device provides an easier and more centralized attachment and eliminates the need for additional attachments.

Another advantage is that the present invention provides an alternative method of attachment to the air/water channel, particularly if the device does not have a gas or $CO_2$ channel. The present invention may provide for attachment to the air/water channel at the air/water control cylinder.

Another advantage is that the present invention reduces the number of attachments that cause additional contamination points. Each additional attachment creates an area between the attachment and the medical device that is difficult to reach with fluid. The more attachments the greater the inconsistency of cleaning and sterilization.

Another advantage is that the present invention uses positive pressure flow. In addition to the improved penetration capabilities previously described, positive pressure flow is easier to provide. Positive pressure provides a greater range of pressures and can be more easily provided through a greater variety of positive pressure pumps. Positive pressure flow provides both the pressure source and the fluid source at one location, simplifying connections and automation. Positive pressure is also safer because contaminates cannot be drawn into the device through leaks in the system.

Another advantage of the present invention is that it may be operated at temperatures less than 50 degrees C. Operating at temperatures below 50 degrees C. prolongs the life of medical devices and reduces burn hazards.

Another advantage is that the present invention may be easily automated. The use of valves controlled by a central processor may be easily automated, particularly in an automatic reprocessing device. The elimination of manually operated equipment and methods such as syringes provides for automation.

These and other objects and advantages of the present invention will become apparent during the course of the following detailed description and appended claims. The invention may best be understood with reference to the accompanying drawings, wherein an illustrative embodiment is shown.

DETAILED DESCRIPTION OF THE INVENTION

General Assembly

Figure 1:
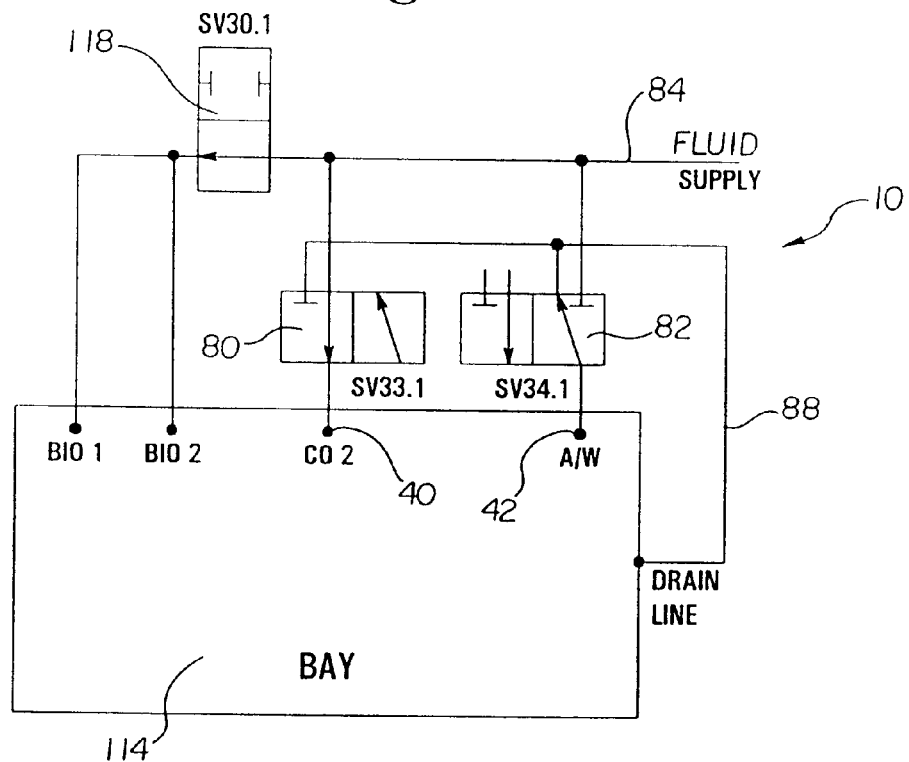
FIG. 1 is a schematic drawing of the device in a first flow position.
Figure 2:
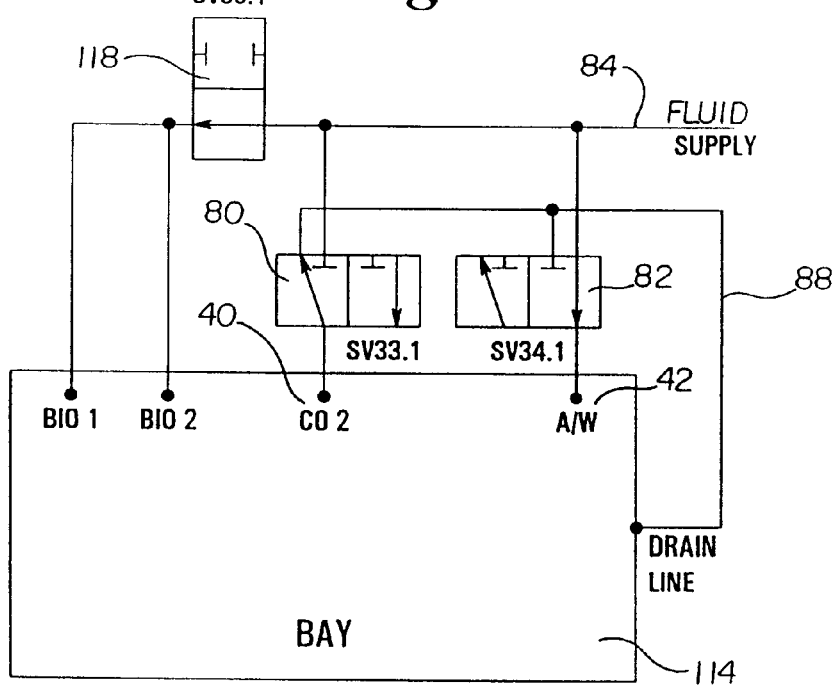
FIG. 2 is a schematic drawing of the device in a second flow position.
Figure 3:
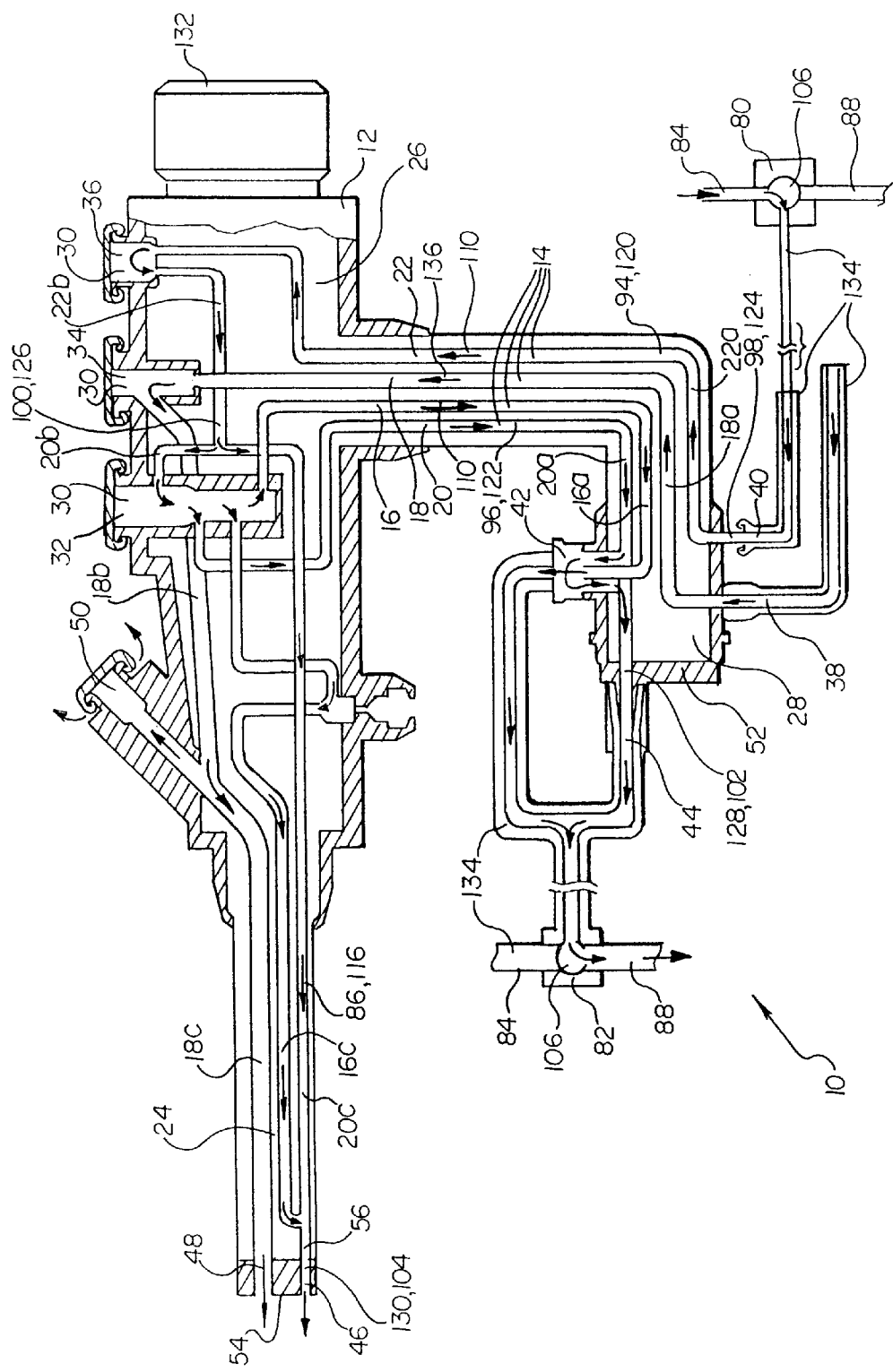
FIG. 3 is a side cross sectional view of an endoscope connected to the device showing a first and a third fluid flow path.
Figure 4:
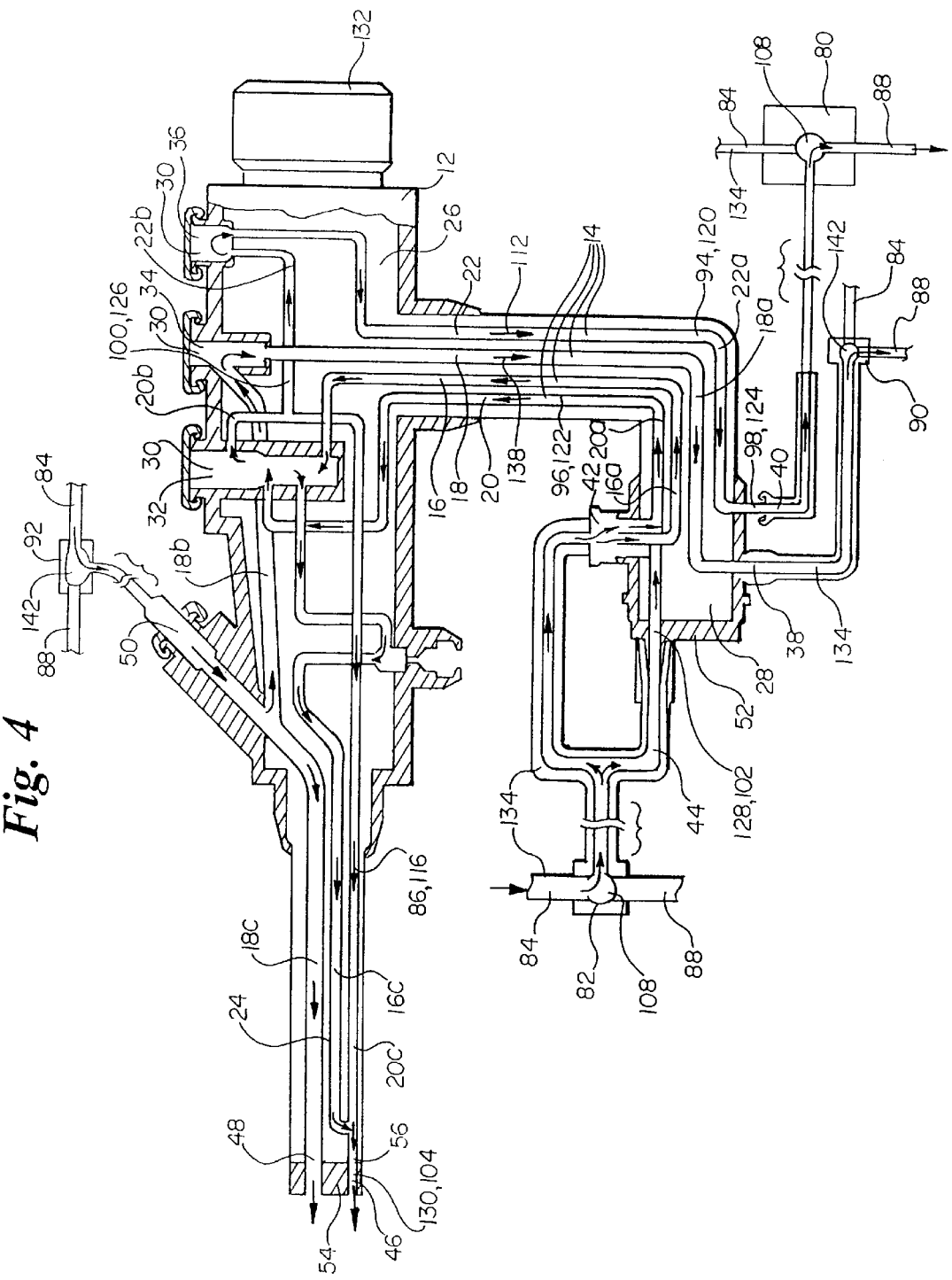
FIG. 4 is a side cross sectional view of an endoscope connected to the device showing a second and fourth fluid flow path.
Figure 5:
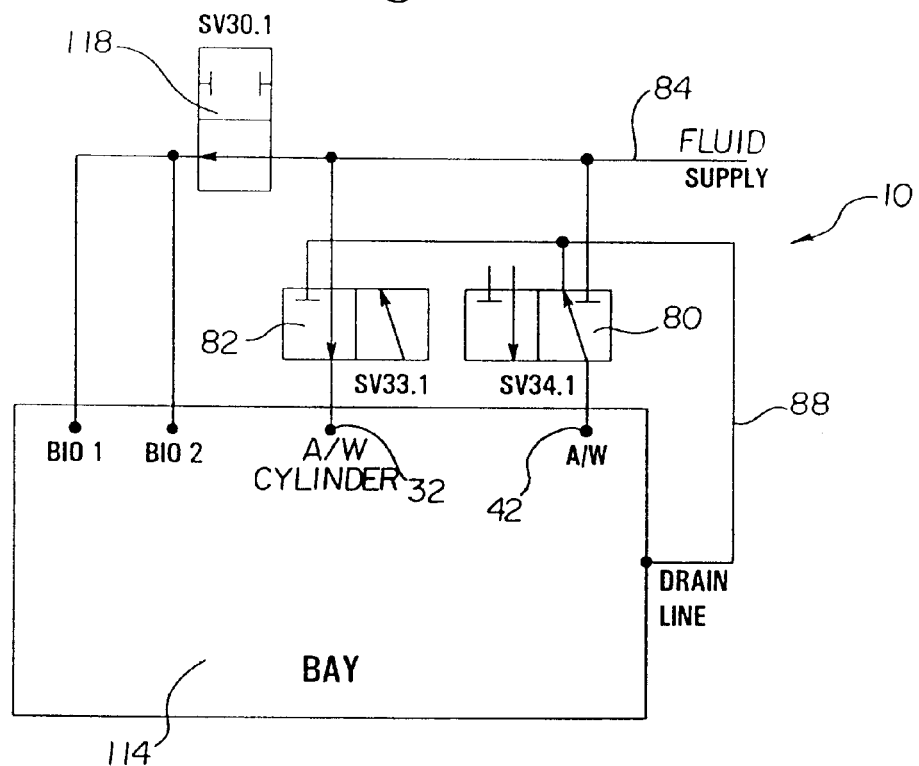
FIG. 5 is a schematic drawing of the device in an alternate second flow position.
Figure 6:
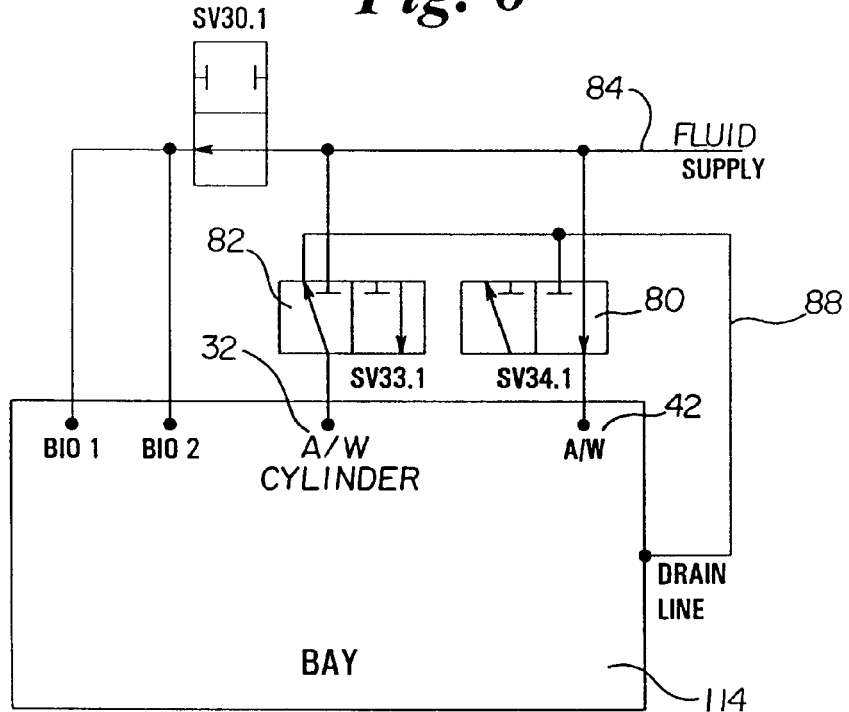
FIG. 6 is a schematic drawing of the device in an alternate first flow position.

Referring to FIGS. 1, 2, 5, 6, 9, and 10, the device 10 in accordance with the present invention broadly includes a first valve 80 and a second valve 82. However, additional valves for additional tubular structures may be provided. The first and second valves 80,82 are each in fluid communication with to a fluid supply 84 at a positive pressure. The first valve 80 is in fluid communication with a first tubular structure 94, the first tubular structure 94 having a proximal end 98 and a distal end 100, the first valve 80 is in fluid communication with the proximal end 98. The tubular structures typically have a length that is about 200 to about 8,000 times the inside diameter. The second valve 82 is in fluid communication with a second tubular structure 96, the second tubular structure 96 having a proximal end 102 and a distal end 104, the second valve 82 is in fluid communication with the proximal end 102. The first tubular structure 94 is in fluid communication with the second tubular structure 96. The first and second valves 80, 82 selectively switch between a first position 106 and a second position 108. In the first position 106, the first valve 80 is open to the fluid supply 84 and the second valve 82 is closed to the fluid supply 84. In the second position 108 the second valve 82 is open to the fluid supply 84 and the first valve 80 is closed to the fluid supply 84. The first position 106 causes a first fluid flow path 110 and the second position 108 causes a second fluid flow path 112. At least a part of the second fluid flow path 112 is opposite the first fluid flow path 110.

The device 10 may also provide that the distal end 100, 104 of at least one of the tubular structures 94,96 is open to a drain 114 at about atmospheric pressure.

The device 10 may also provide that in the first position 106 the second valve 82 is open to the drain line 88 and in the second position 108 the first valve 80 is open to the drain line 88.

The device 10 may also provide that the fluid supply 84 has a flow volume from preferably about 100 ml/min to about 1400 ml/min. Preferably the flow volume is about 100 ml/min to about 250 ml/min for tubular structures of about 1 mm to about 2 mm in diameter and about 600 ml/min to about 1400 ml/min for tubular structures of about 3 mm to about 6 mm in diameter. The fluid supply 84 has a flow velocity from preferably about 50 cm/sec to about 500 cm/sec and most preferably about 50 cm/sec to about 250 cm/sec. The fluid supply 84 has a pressure preferably below about 20 psi and most preferably from about 10 psi to about 20 psi. Pressures above about 20 psi may damage the endoscope and are not recommended by manufacturers. The sterilizing fluid 116 is preferably provided for about 1 minute to about 20 minutes and most preferably about 10 minutes.

The device 10 may also provide a third and a fourth valve, a third and a fourth tubular structure, and a third and a fourth position.

The device 10 may also be used in an automatic reprocessing device so that a central processor controls positioning of the valves.

The device 10 may be used to process a medical device with lumens such as an endoscope 12 described below. Endoscopes may be about 1 m to about 4 m long and have lumens ranging from about 0.5 mm to about 6 mm.

As shown in FIGS. 3,4 7, and 8, endoscope 12 may have a plurality of tubular structures or lumens 14. The lumens 14 typically consist of a water channel 16, a suction channel 18, an air channel 20, and a $CO_2$ channel 22. The endoscope 12 typically has an insertion section 24 extending from a control section 26 and an umbilical section 28 also extending from the control section 26. The lumens 14 are defined inside the endoscope 12 and extend through the endoscope 12 from the insertion section 24 and are in fluid communication with control valve cylinders 30 and extend and are in fluid communication with the lumens 14 in the umbilical section 28. There are typically three control valve cylinders 30 including an air/water cylinder 32, a suction cylinder 34, and a $CO_2$ cylinder 36.

Umbilical Section

During use, the light guide or umbilical section 28 of the endoscope 12 connects the lumens 14 of the endoscope 12 to a supply of air, water, and $CO_2$ via supply ports located at the distal end 52 of the umbilical section 28. The lumens 14 include an air channel 20, a suction channel 18, a water channel 16 and a $CO_2$ channel 22. The umbilical section has a suction supply port 38 in fluid communication with the suction channel 18, a $CO_2$ supply port 40 in fluid communication with the $CO_2$ channel 22, an air supply port 44 in fluid communication with the air channel 20, and an air/water supply port 42 in fluid communication with the water channel 16 and the air channel 20. The lumens 14 extend through the umbilical section 28 and are in fluid communication with the control cylinders 30 located in the control section 26.

Control Section

The control section 26 is located in the middle of the endoscope 12 and contains the control cylinders 30 and the lens 132 for viewing though the endoscope 12. During normal operation, the control cylinders 30 contain control valves and provide operational control of the flow of air, water, and $CO_2$. During processing, cleaning, and sterilization, the control valves are removed from the air/water control cylinder 32 and the suction cylinder 34 and the openings are capped. The $CO_2$ control valve in the $CO_2$ cylinder 36 is left in the open position. The $CO_2$ cylinder 36 is in fluid communication with both the $CO_2$ channel 22 from umbilical section 28 and the $CO_2$ channel 22 that is in fluid communication with the air channel 20 between the air/water cylinder 32 and the insertion section 24. The air/water cylinder 32 is in fluid communication with four channels, a) the air channel 20 from the umbilical section 28, b) the water channel 16 from the umbilical section 28, c) the air channel 20 from the insertion section 24, and d) the water channel 16 from the insertion section 24. The insertion section 24 typically has three instead of four lumens because the $CO_2$ channel 22 joins and is in fluid communication with the air channel 20 in the control section 26 downstream of the control cylinders 30.

Insertion Section

The insertion section 24 is connected to the control section 26 of the endoscope 12 and is the portion of the endoscope 12 that is inserted into the patient during use. The insertion section 24 has an air/water nozzle 46 and a suction opening 48 located at the distal end 54 of the insertion section 24. The water channel 16 and air channel 20 merge in the insertion section 24 to form an air/water channel 56. The air/water channel 56 is in fluid communication with the air channel 20 and the water channel 16 and with the air/water nozzle 46. The air channel 20 is in fluid communication with the air/water cylinder 32 and with the air/water channel 56. The water channel 16 is in fluid communication with the air/water cylinder 32 and with the air/water channel 56. The suction channel 18 is in fluid communication with the suction cylinder 34 and with the suction opening 48. The endoscope may also have a forceps or biopsy port 50 located in the control section 26. The biopsy port 50 is in fluid communication with the suction channel 18 between the suction cylinder 34 and the suction opening 48.

Suction Channel

The suction channel 18 is typically from about 3 mm to about 6 mm in diameter. The suction channel 18 can be subdivided into an umbilical suction channel 18a, a control suction channel 18b and an insertion suction channel 18c. The umbilical suction channel 18a is the portion of the suction channel 18 from the suction supply port 38 to the suction cylinder 34. The control suction channel 18b is the portion from the suction cylinder 34 to the biopsy port 50. The insertion suction channel 18c is the portion from the biopsy port 50 to the suction opening 48.

Air Channel

The air channel 20 is typically from about 1 mm to about 2 mm in diameter. The air channel 20 can be subdivided into an umbilical air channel 20a, a control air channel 20b, and an insertion air channel 20c. The umbilical air channel 20a is the portion from the air/water supply port 42 and the air supply port 44 to the air/water cylinder 32. The control air channel 20b is the portion from the air/water cylinder 32 to the $CO_2$ channel 22. The insertion air channel 20c is the portion from the $CO_2$ channel 22 to the air/water channel 56.

Water Channel

The water channel 16 is typically from about 1 mm to about 2 mm in diameter. The water channel 16 can be subdivided into an umbilical water channel 16a and an insertion water channel 16c. The umbilical water channel 16a is the portion from the air/water supply port 42 to the air/water cylinder 32. The insertion water channel 16c is the portion from the air/water cylinder 32 to the air/water channel 56.

$CO_2$ Channel

The $CO_2$ channel 22 is typically from about 0.5 to about 2 mm in diameter. The $CO_2$ channel 22 is particularly complex and restricted in the $CO_2$ valve. The $CO_2$ or gas valve utilizes narrow passages and restrictions. The $CO_2$ channel 22 may be subdivided into an umbilical $CO_2$ channel 22a, and a control $CO_2$ channel 22b. The umbilical $CO_2$ channel 22a is the portion from the $CO_2$ supply port 40 to the $CO_2$ cylinder 36 and the control $CO_2$ channel 22b is the portion from the $CO_2$ cylinder 36 to the air channel 20.

The Device

As previously described and as shown in FIGS. 1 through 10, the device 10 broadly includes a first valve 80 and a second valve 82. The first and second valves 80, 82 are each in fluid communication with a fluid supply 84.

In the preferred connection to an endoscope, the first valve 80 is in fluid communication with the $CO_2$ supply port 40 and the second valve 82 is in fluid communication with the air/water supply port 42. The connection to the air/water supply port 42 may also preferably include a connection to the air supply port 44 using a T-connection. In addition, either valve 80, 82 may be connected to either the $CO_2$ supply port 40 or the air/water supply port 42.

In an alternative connection to an endoscope, the first valve 80 is in fluid communication with the air/water supply port 42 and the second valve 82 is in fluid communication with the air/water cylinder 32. The connection to the air/water supply port 42 may also include a connection to the air supply port 44 using a T-connection. In addition, either valve 80, 82 may be connected to either the air/water cylinder 32 or the air/water supply port 42.

The valves 80, 82 are preferably three-way valves that provide three connections to the valve and allow flow between any two connections. However, the valves may be two-way valves or a combination of two-way valves. Preferably one connection is in fluid communication with the fluid supply 84, a second connection is connected to a first tubular structure 94, and one connection is connected to a second tubular structure 96. The valves 80, 82 are preferably Predyne B3314 three way valves with ⅛ inch NPT threads and a fluid constant (Cv) of 0.11. The valves 80, 82 may be in fluid communication with the tubular structures 94, 96 by any means known in the art such as tubing and flexible couplings.

The connecting lines 134, including the fluid supply 84 and the drain line 88 may be of any material used in sterilizing and cleaning processing equipment. The connecting lines are preferably about ¼ inch to about ½ inch diameter plastic tubing, preferably polyethylene.

The device 10 may also include a blocking valve 118 in the fluid supply 84 to direct the flow of fluid to a limited number of tubular structures. Limiting the flow to one or two lumens allows the use of a smaller fluid supply pump. Limiting the flow to one lumen at a time also assures that each lumen receives adequate flow and is not affected by different lumen sizes or by blockages. The blocking valve 118 may also be used in testing procedures to determine if blockages exist in the lines or lumens.

The fluid may consist of a cleaning fluid 86, a sterilizing fluid 116, or any other fluid that is desired to reach all portions of the tubular structure 94,96. The fluid may be a liquid or a gas. The sterilizing fluid 116 may comprise a liquid performic acid based sterilant, as described in provisional application 60/102,664 entitled MULTI-PART ANTI-MICROBIAL CONCENTRATE SYSTEM ACTIVATED FLUID, USE-DILUTION FLUID, METHOD OF MAKING SAME, AND METHOD OF STERILIZING WITH THE USE-DILUTION FLUID, filed on Oct. 1, 1998, the disclosure of which is hereby incorporated by reference.

The device and method of the present invention may be incorporated into an endoscope reprocessing device, as described in provisional application 60/102,663 entitled ENDOSCOPE REPROCESSING AND STERILIZATION SYSTEM, filed on Oct. 1, 1998, the disclosure of which is hereby incorporated by reference. FIGS. 11–16 and the following description of the medical reprocessing device are from the above described provisional application.

Automatic Medical Instrument Reprocessing Device

Figure 11:
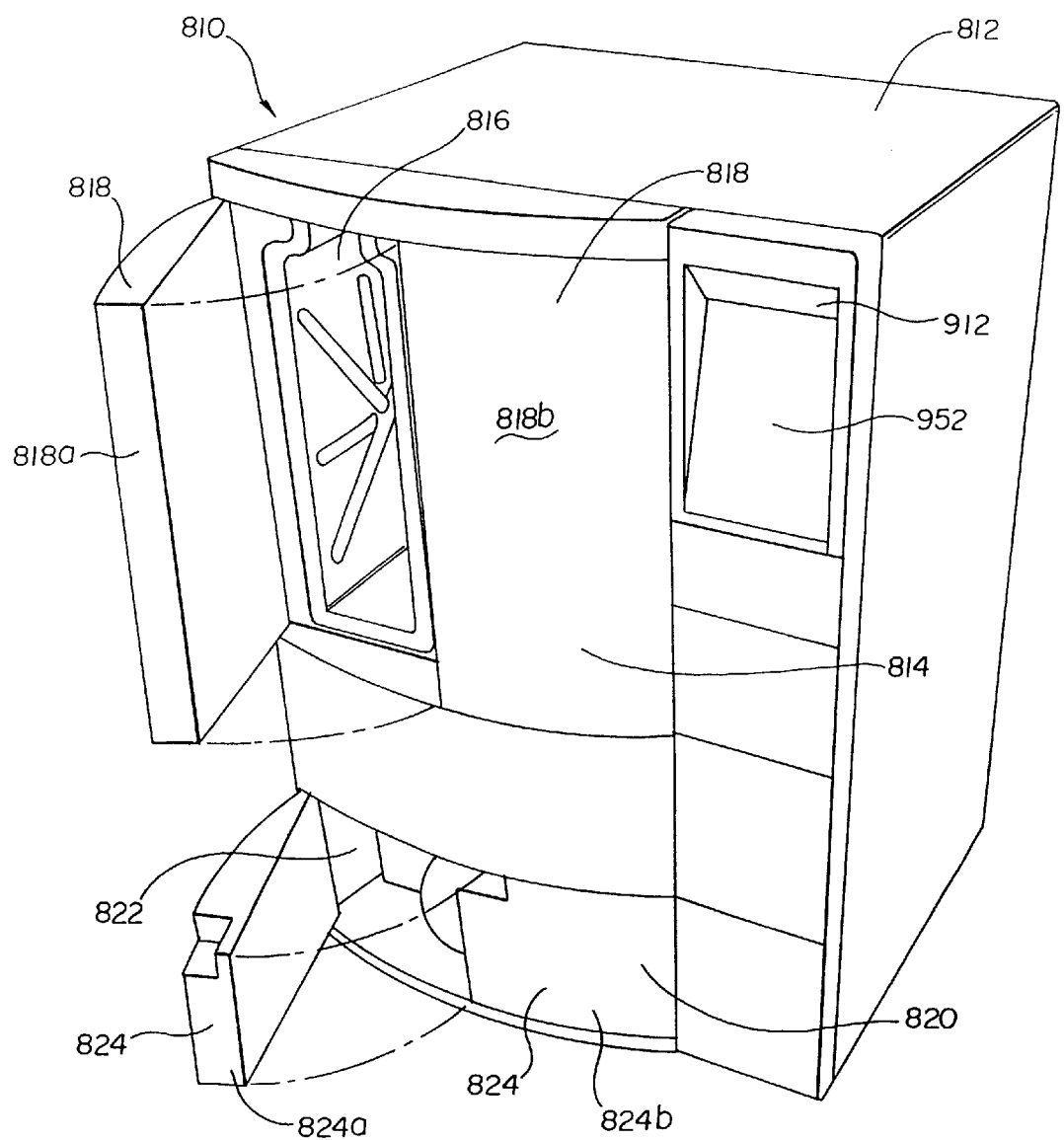
FIG. 11 shows an exterior perspective view of a medical instrument reprocessing device having one of a pair of chemical supply drawer access doors in an open position and one of a pair of reprocessing bay cabinet access doors in an open position.
Figure 12:
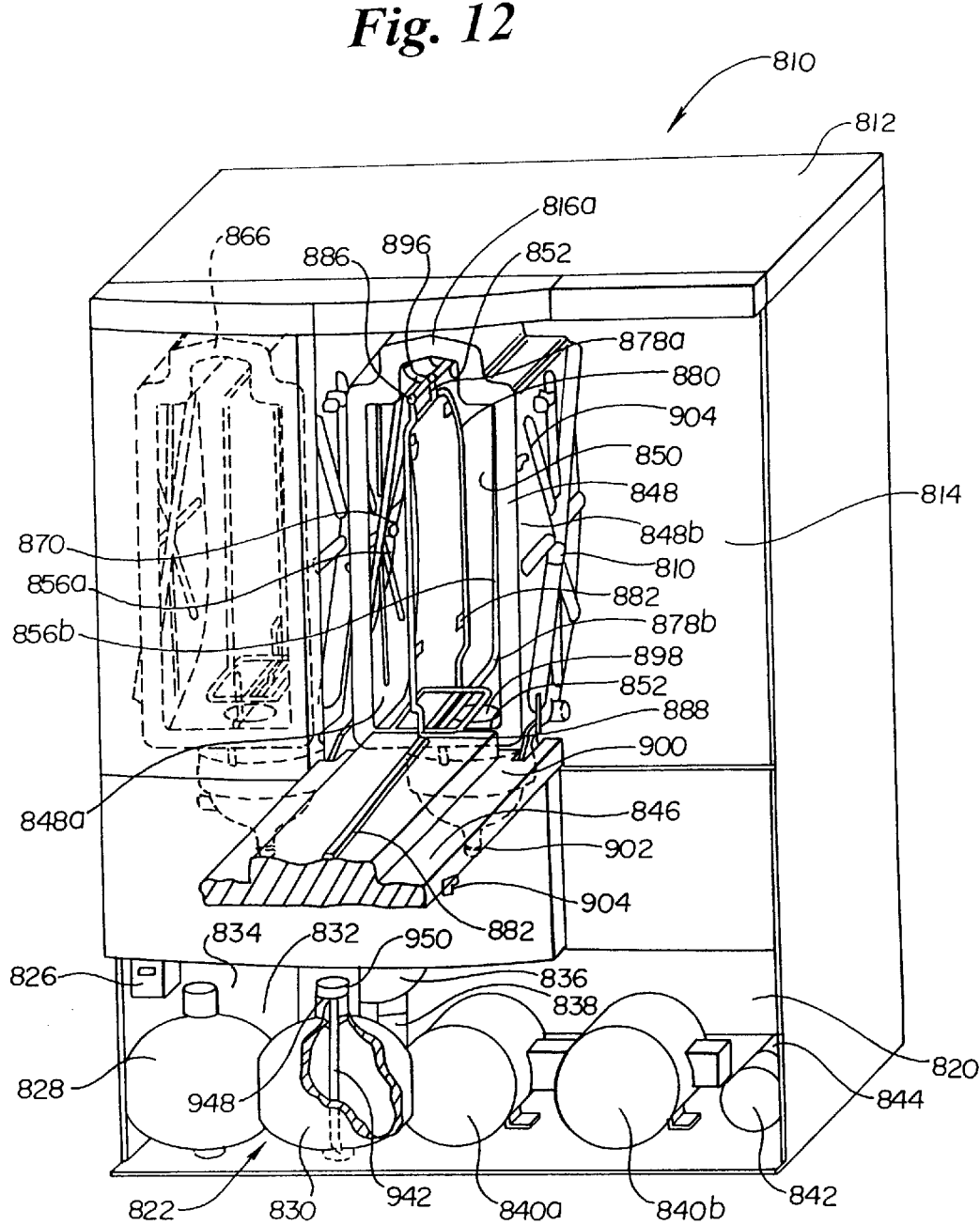
FIG. 12 shows a perspective view of the major components of a medical instrument reprocessing device in one possible arrangement relative to each other and positioned in a representation of the compartmentalization provided by an exterior housing. Two reprocessing bays are represented in the reprocessing bay cabinet of the housing; one configured with a reprocessing bay door in the open position and the other, presented in broken lines, configured without the necessary reprocessing bay door.

Referring now to FIGS. 11–15, an endoscope reprocessing and sterilization system is shown and generally indicated as 810. An exterior housing 812 is provided to arrange, contain and provide protection for the components of the reprocessing system 810. A reprocessing bay cabinet 814 of the housing 812 is configured to contain at least one reprocessing bay 816. The reprocessing bay cabinet 814 is equipped with at least one cabinet access door 818. The embodiment shown in FIG. 11 is configured to have two cabinet access doors 818a, 818b which are shown with one cabinet access door 818a in the open position allowing access to the at least one reprocessing bay 816 and the other cabinet access door 818b in the closed position. The preferred embodiment shown in FIGS. 11–12 is configured to have two independently operated reprocessing bays 816a, 816b, although it is not limited to two independently operated reprocessing bays 816.

A chemical supply drawer 820, which is configured to contain support components, generally indicated at 822, is equipped with at least one drawer access door 824.

The embodiment shown in FIG. 11 is configured to have two chemical supply drawer access doors 824a, 824b which are shown with one drawer access door 824a in the open position allowing access to the support components 822 and the other drawer 820 access door 824b in the closed position. The support components 822, contained within the chemical supply drawer 820, can include a soap container 826, a plurality of chemical sterilant component containers 828, 830, a water heater 832, a hot water tank 834, a reaction chamber 836, a load sensor 838, an electric motor and pump 840, an air compressor 842, and a compressed air tank 844. The preferred embodiment shown in FIG. 12 is configured with two chemical sterilant component containers 828, 830 which serve to contain the two components of a multi-component concentrate system. The reprocessing system 810 may include a greater or lesser number of chemical sterilant component containers depending upon the number of components required for the sterilant used. In the preferred embodiment, each of the two reprocessing bays 816a, 816b is independently operated. To support such independent operation, the device 810, as shown in FIG. 12, is equipped with an independently operated electric motor and pump 840a, 840b, one for each reprocessing bay 816a, 816b.

Figure 15:
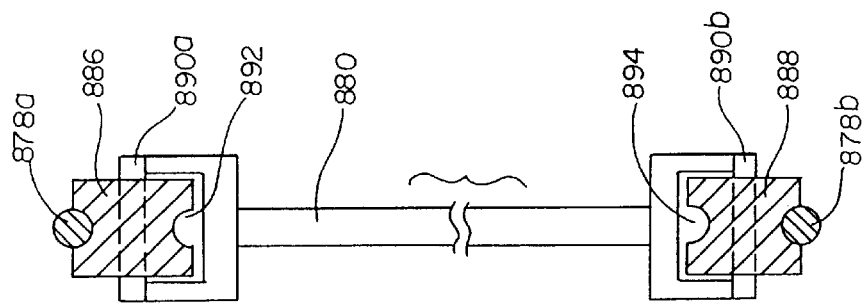
FIG. 15 shows a front elevational view of the movable cassette assembly of a medical instrument reprocessing device.
Figure 14:
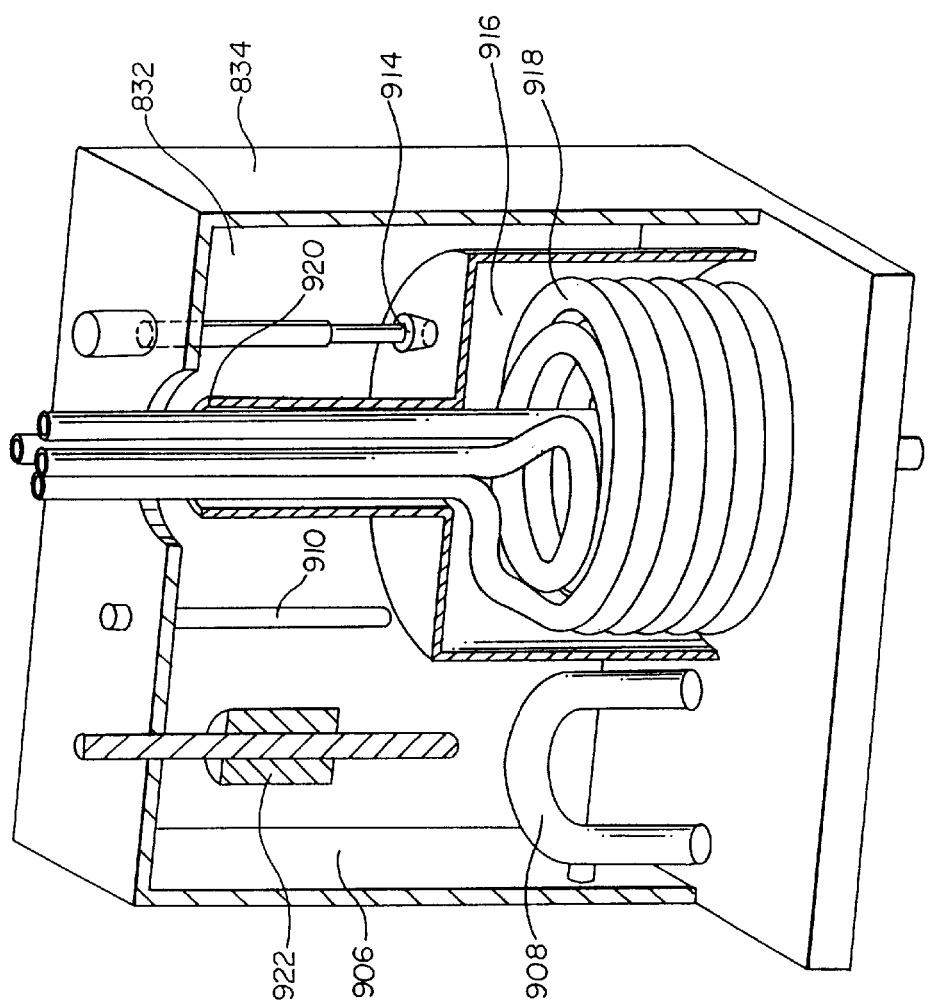
FIG. 14 shows a perspective sectional view of a heater assembly of a medical instrument reprocessing device invention.
Figure 16:
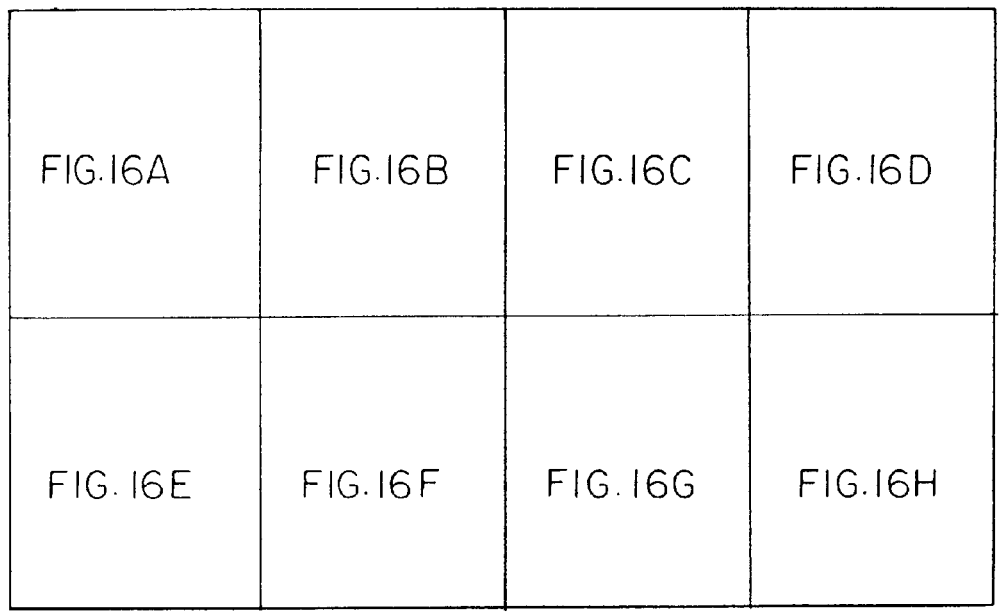
FIG. 16 shows a schematic representation of the hydraulic system and pneumatic system of a medical instrument reprocessing device.
Figure 16A:
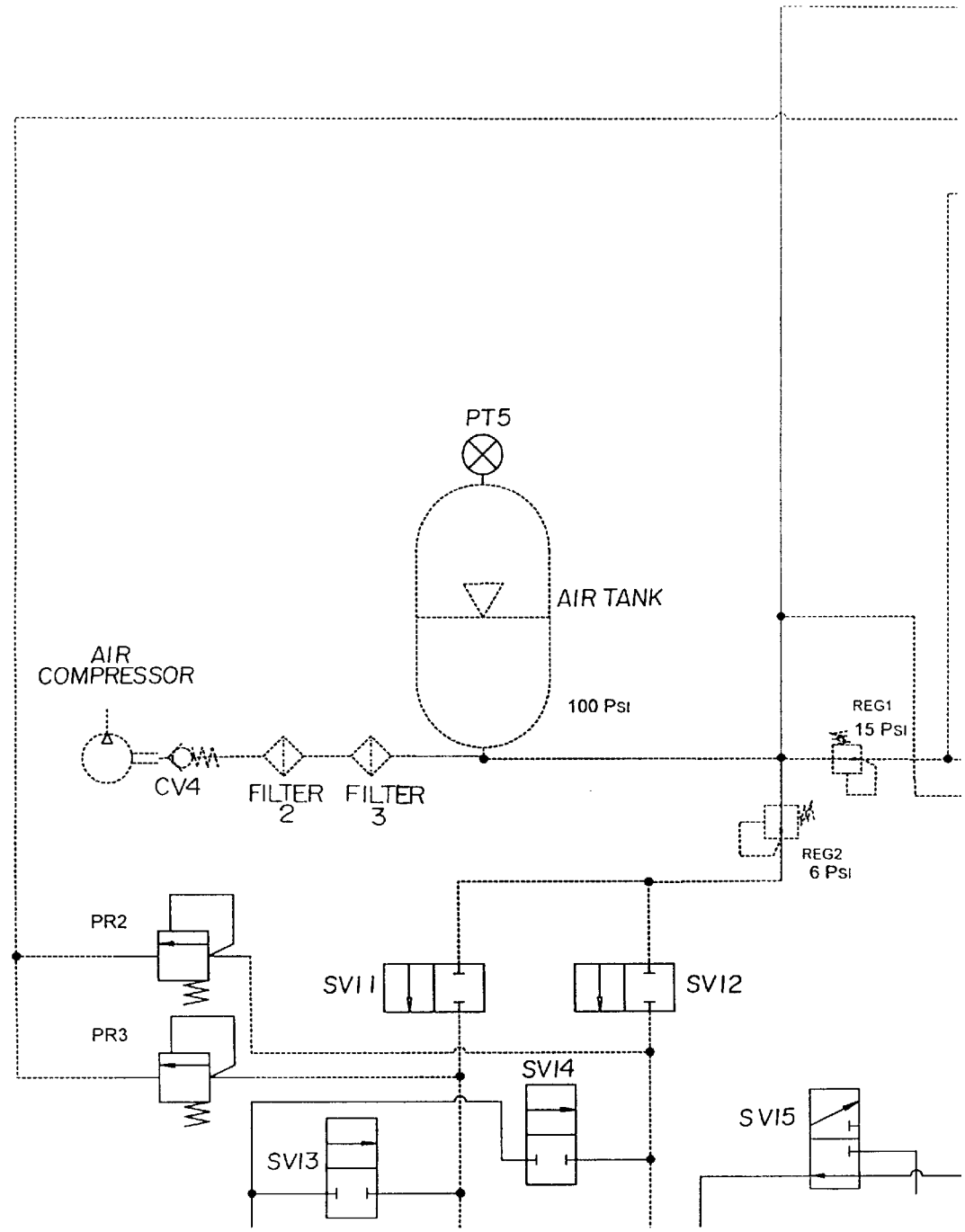
Figure 16B:
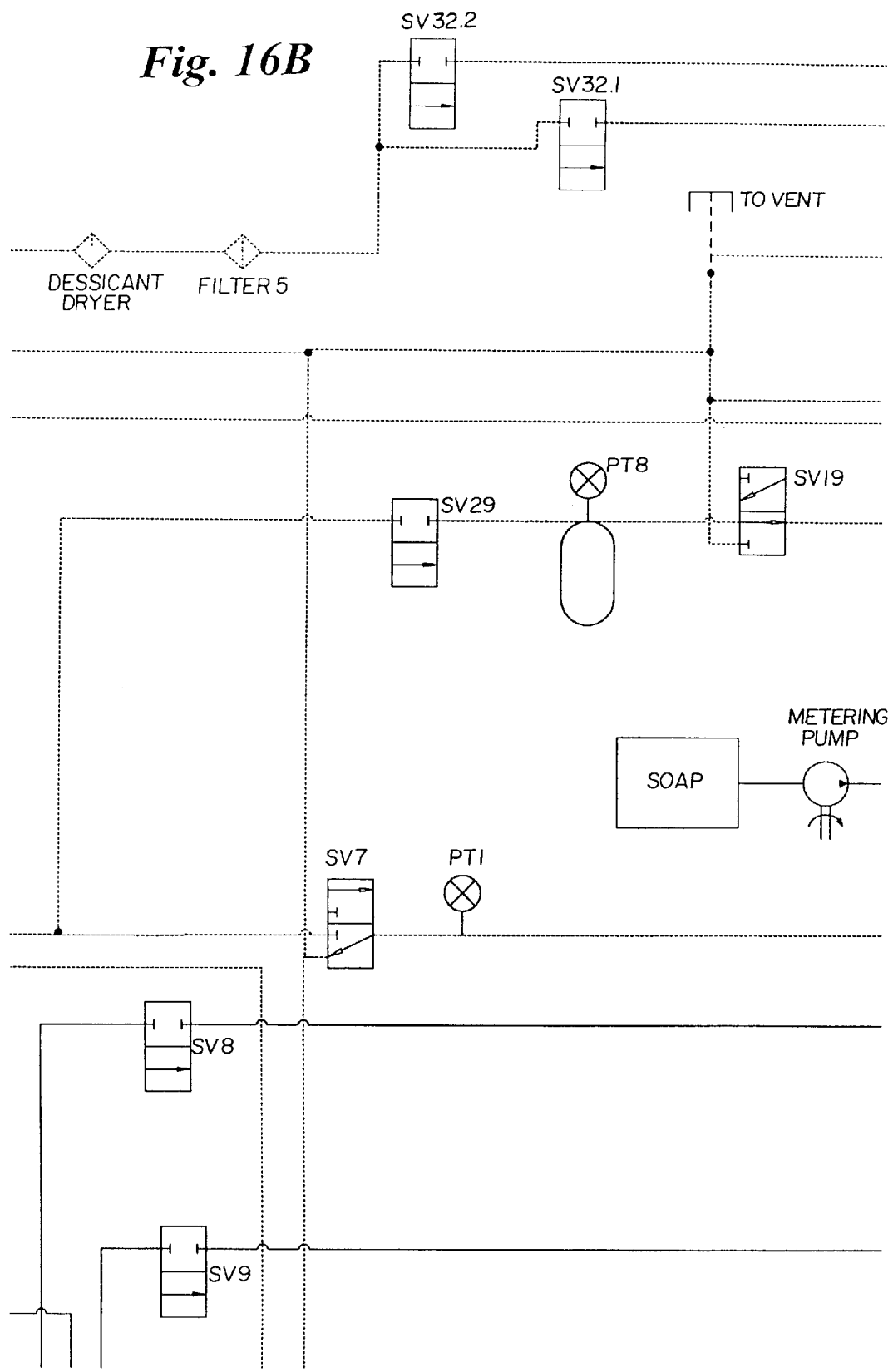
Figure 16C:
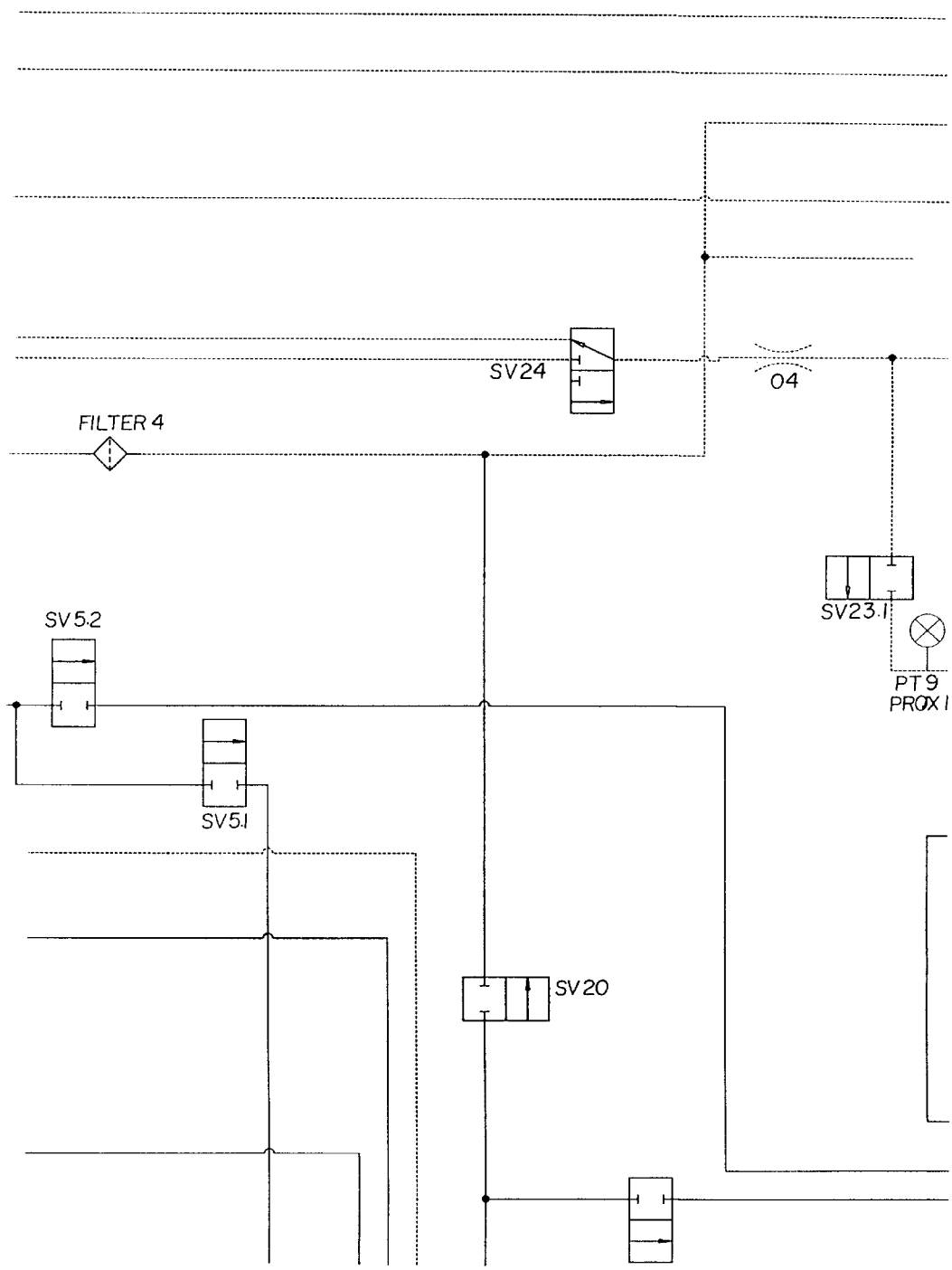
Figure 16D:
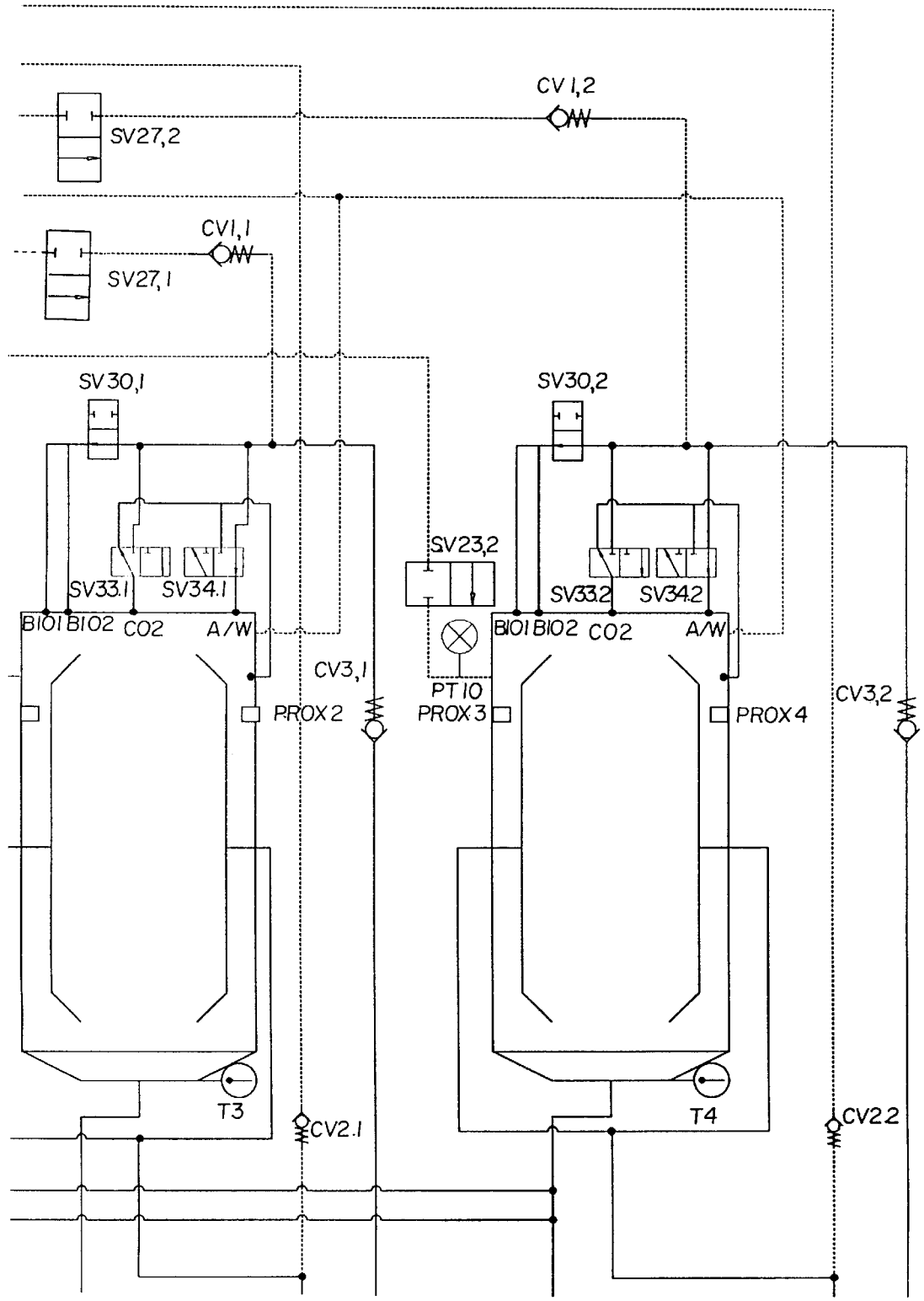
Figure 16E:
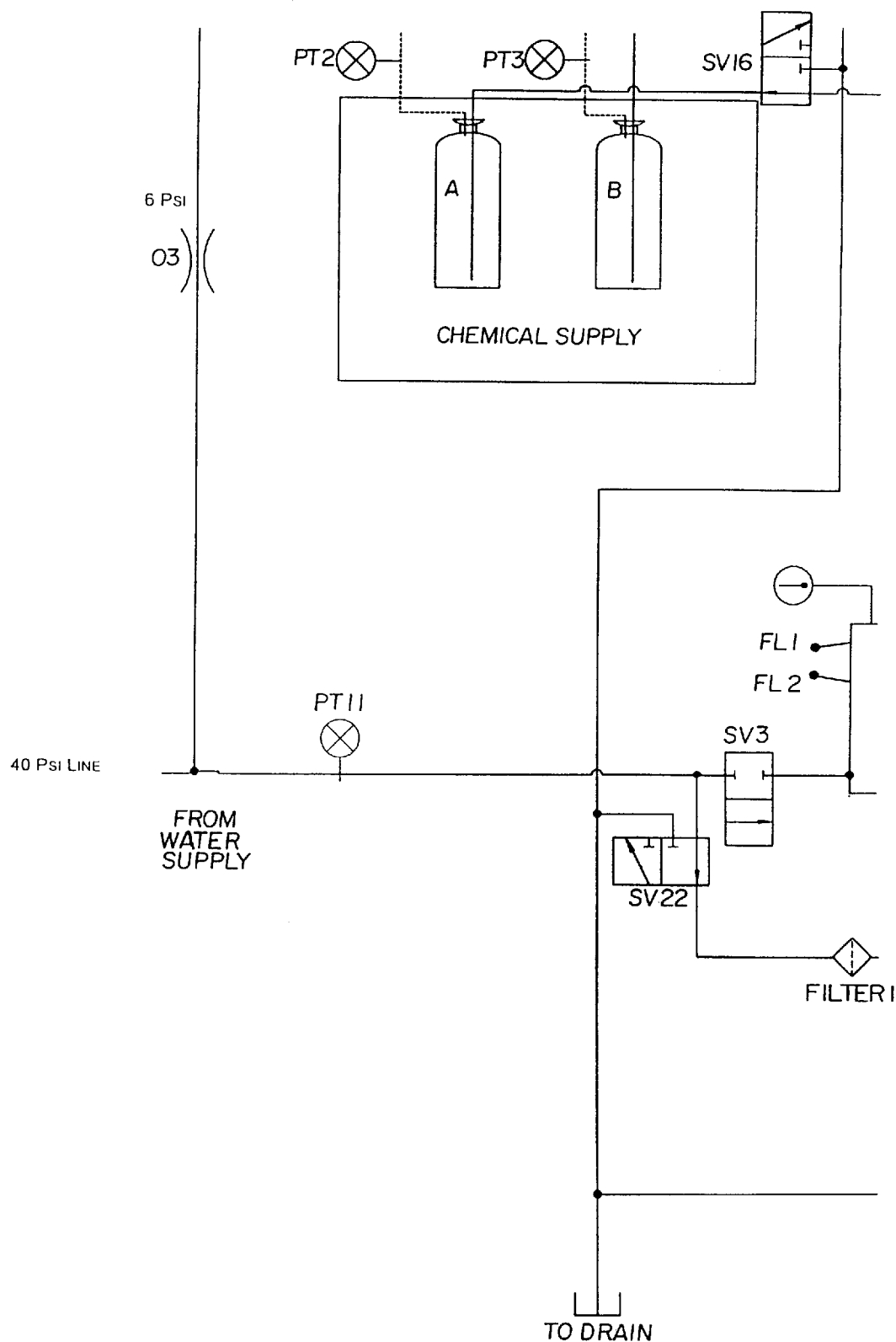
Figure 16F:
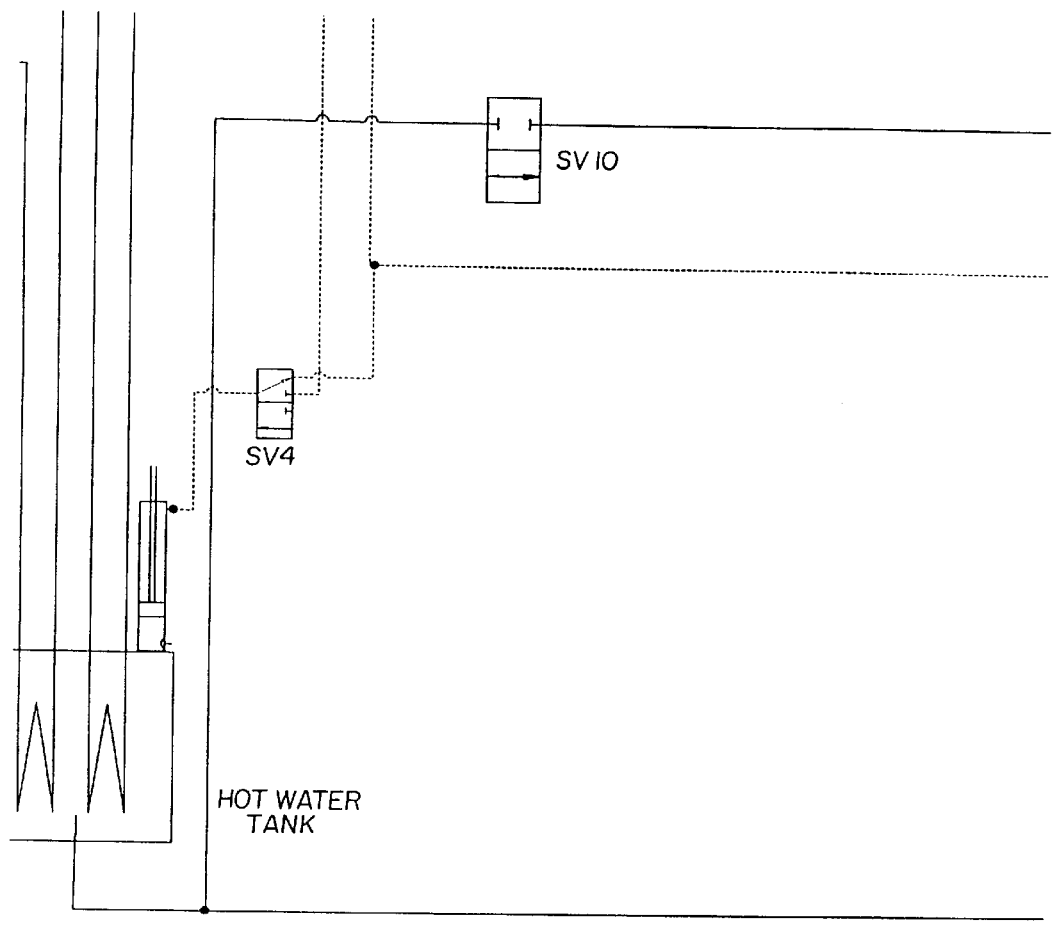
Figure 16H:
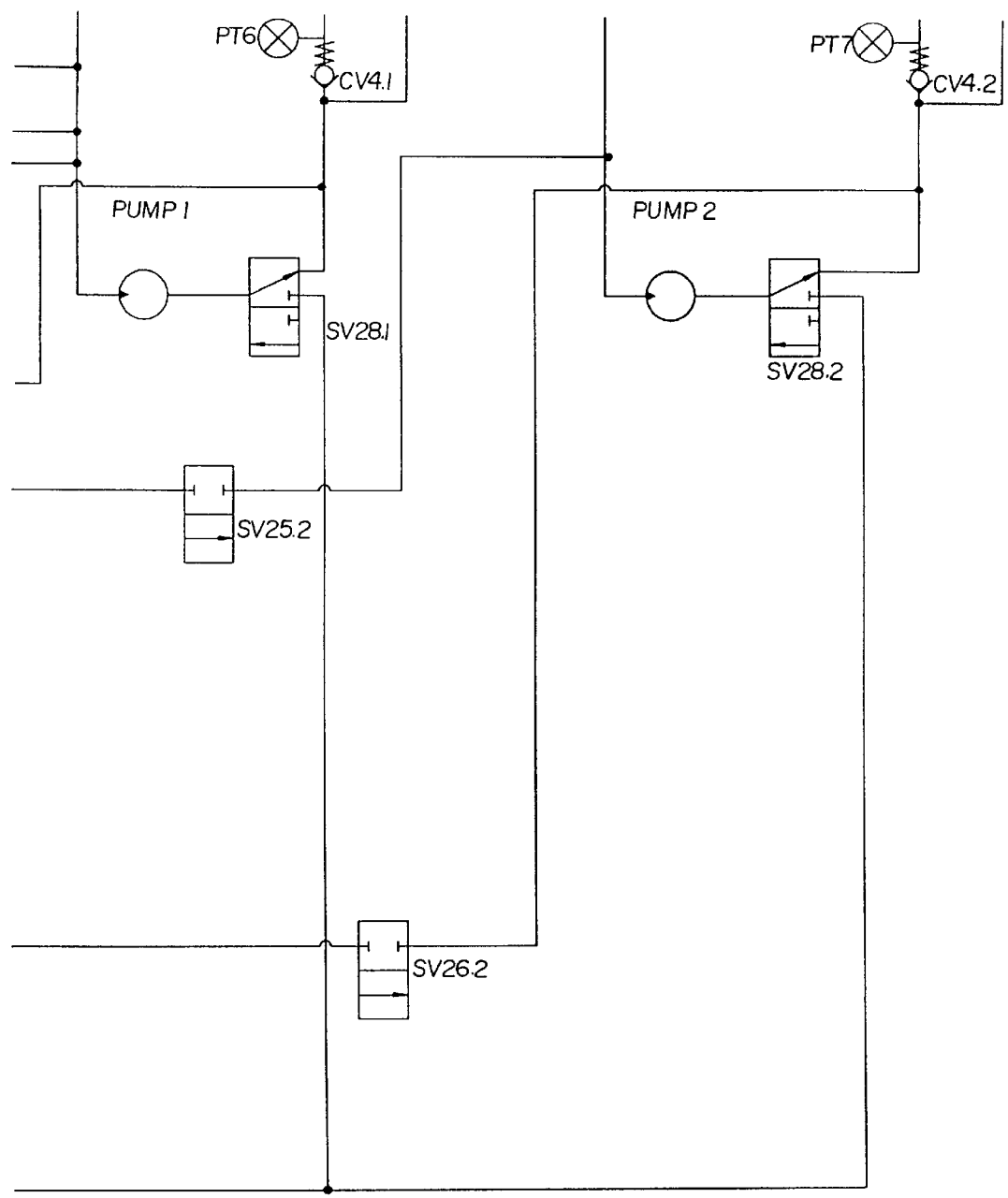

Hydraulic and pneumatic connections between each of the components contained within the chemical supply drawer 820 and the reprocessing bays 816a, 816b contained within the reprocessing bay cabinet 814 are shown only in FIG. 16 to simplify presentation of the major components shown in FIGS. 11–15.

The reprocessing bays 816a, 816b are identically configured and independently operated. Detail discussion of the reprocessing bay components and operations will, for demonstration purposes, be limited to descriptions of reprocessing bay 816a.

The reprocessing bay 816a is equipped with a reprocessing bay door 846, which serves to seal the reprocessing bay during operation. The reprocessing bay door 846 can be constructed so as to provide thermal and sound proofing features. The vertical side walls 848a, 848b, back wall 850, ceiling member 852, and floor member 854 can also be formed to provide thermal and sound proofing features. The thermal and sound proofing features can be provided by manufacturing the side walls 848a, 848b, back wall 850, ceiling 852, floor 854, and door 846 structures of materials such as, for example, plastics, steel, glass, and the like.

Figure 13:
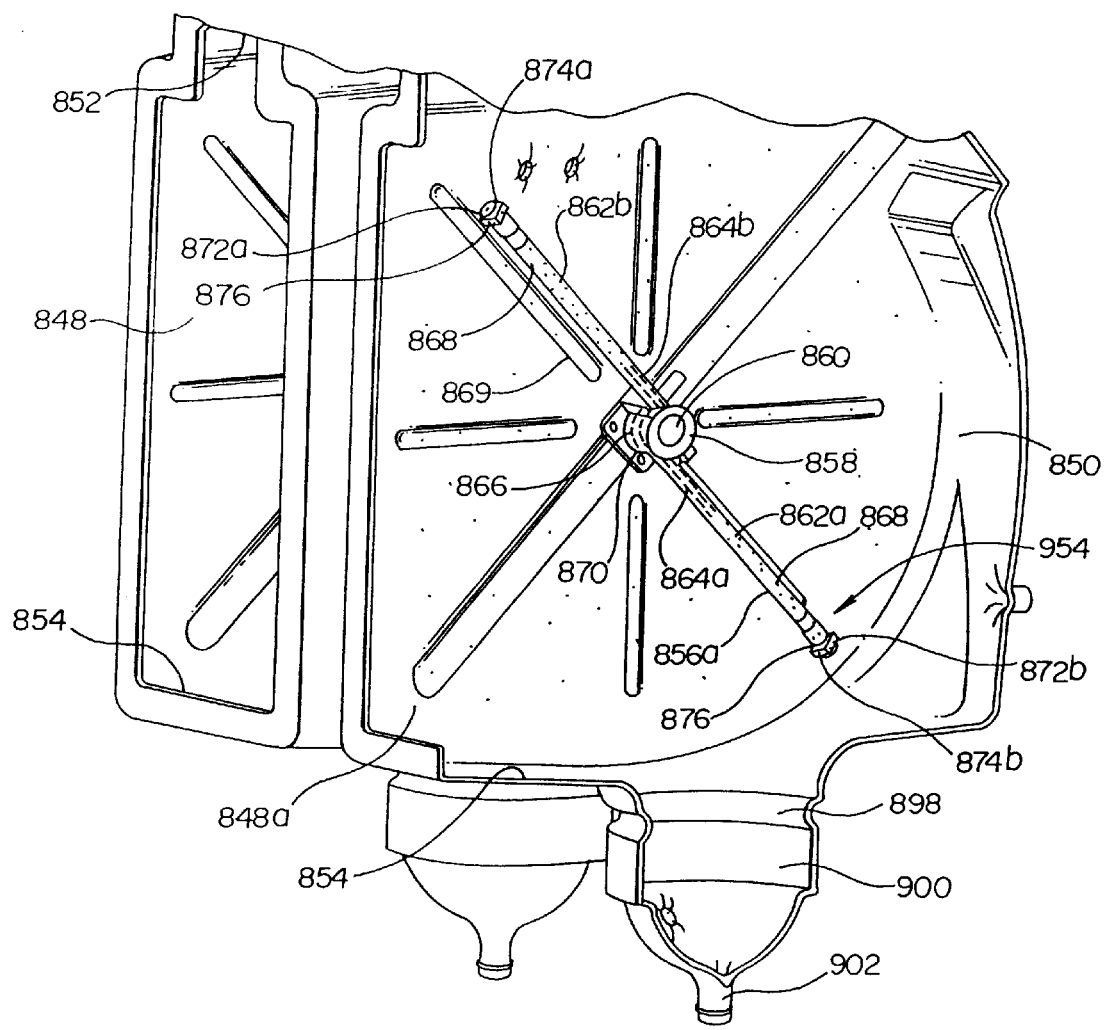
FIG. 13 shows a perspective view of two reprocessing bays, without access panels, of a medical instrument reprocessing device. One reprocessing bay is shown in a partial sectional view disclosing an exterior pressure washing assembly.

The reprocessing bay 816a is equipped with at least one and preferably two identical rotating arm members 856. In the preferred embodiment, the two rotating arm members 856a, 856b are separately rotatably mounted on a central portion of opposing side walls 848a, 848b. The following detailed description applies to all rotating arm members 856 but reference is limited to rotating arm member 856a, which is best shown in FIG. 13. The rotating arm member 856a includes a central hub sleeve 858 rotatably connected around a rotating arm hub member 860 which extends outwardly at about a right angle from the central portion of side wall 848a. At least two counterbalanced spray arms 862a and 862b are connected on approximate opposing sides of the central hub sleeve 858. Each spray arm 862a, 862b defines a spray arm lumen 864a, 864b (shown in part with broken lines). The spray arm lumen 864a, 864b extends at least a portion of the length of the spray arm 862a, 862b and serves to operatively connect a hub sleeve lumen 866 defined within the central hub sleeve 858 with a plurality of spray jets 868 defined in the wall of the spray arms 862a, 862b. Together the interconnected hub sleeve lumen 866, spray arm lumens 864a, 864b and spray jets 868 provide a conduit for the pressurized flow of washing, rinsing and sterilizing fluids from a rotating fluid connector 870, defined within the hub member 860, to the interior of the reprocessing bay 816a. The washing, rinsing and sterilizing fluids are provided to the rotating fluid connector 870 by tubular conduits as shown in FIG. 16. Optionally, one or more of the side walls 848a, 848b, back wall 850, ceiling 852, floor 854 and door 846 members walls of the reprocessing bay can be provided with wall spray jets 869 which are fluidly connected to the rotating fluid connector 870 or, alternatively, to a separate fluid inlet connector. Tubular conduits used in the present invention can be formed of metal, plastic, glass and the like as is well known in the art.

At the each distal end 872a, 872b of spray arms 862a, 862b is a spray nozzle 874a, 874b, which is configured with a plurality of spray openings 876. The spray openings 876 are operatively connected to the spray arm lumens 864a, 864b and together with the spray jets 868 direct sterilant and rinse fluids into the central portion of the reprocessing bay 816a. Spray nozzles 874a, 874b may also rotate about the longitudinal axis of spray arms 862a, 862b. In addition to the fluid directing function for sterilizing and rinsing, the spray openings 876 and spray jets 868 direct the pressurized flow of fluid out of the spray nozzle 874a, 874b and spray arms 862a, 862b in such a manner as to effect aggregate impulse which produces a reactive rotational force of the spray arms 862a, 862b around the central hub 860.

The reprocessing bay 816a can have at least one cassette guide 878 which serves to guide a cassette 880 from a loading position outside of the reprocessing bay 816a to an operational position inside the reprocessing bay 816a. Preferably the reprocessing bay 816a is equipped with two cassette guides, an upper cassette guide 878a and a lower cassette guide 878b. The upper cassette guide 878a can be secured to the ceiling 852 or alternatively to the upper portion of the back wall 850 of reprocessing bay 816a. The lower cassette guide 878b can be secured to the floor 852 or alternatively the lower portion of the back wall 850 of reprocessing bay 816a. The interior surface of the door 846 of reprocessing bay 816a can be configured to have a door guide 882 which aligns with the lower cassette guide 878b to facilitate the positioning of the cassette 880 into or out of the reprocessing bay 816a.

The cassette 880 is configured to removably secure a medical device such as an endoscope within the reprocessing bay 816a. The medical device is preferably suspended above the washing, rinsing or sterilizing fluid. The cassette 880 can be equipped with a plurality of clamping members 882 for holding the medical device being sterilized in position in the reprocessing bay 816a. The cassette can be removably positioned in the reprocessing bay 816a in a suspended orientation to the upper cassette guide 878a. As best shown in FIGS. 12 and 15, the cassette is preferably removably positioned between the upper cassette guide 878a and the lower cassette guide 878b. As best shown in FIG. 15, the cassette 880 can be configured to have an upper rotational member 886 and a lower rotational member 888 which are independently able to freely rotate about an axle member 890a, 890b which is fixedly secured to the upper and lower portions of the cassette 880. The upper rotational member 886 and the lower rotational member 888 are each provided with a guiding groove 892, 894, respectively. The guiding grooves 892, 894 are sized and configured to complement the size and shape of the upper cassette guide 878a and the lower cassette guide 878b, respectively, for purpose of facilitating ease of movement of the cassette into and out of the reprocessing bay 816a.

In addition, the guiding groove 894 is sized and configured to complement the door guide 882 size and shape so as to guide and facilitate movement of the lower rotational member 888 across the inner surface of the reprocessing bay door 846 when the bay door 846 is in the open position.

Extending into the upper portion of the reprocessing bay 816a is a medical device connector 896 which is configured to provide a fluid tight fitting for a wide variety of medical devices, such as endoscopes. It is within the concept of the present invention to provide connection adapters that will permit a fluid tight fitting during pressure sterilization of the lumen of a wide variety of medical devices. Washing, rinsing and sterilizing fluids are provided to the medical device connector through tubing conduits as shown in FIG. 16.

The floor member 854 of the reprocessing bay 816a is configured to serve as a reservoir 898 for collection of fluids which have been sprayed onto or through the medical device being reprocessed and sterilized in the reprocessing system 810. The reservoir can be equipped with a filtration system 900 of at least two levels of filtration. A sump drain 902 for collection of fluids is provided in the lower portion of the reservoir 898. The size of the reservoir 898 and the vertical positioning of the reprocessing bays 816 allows the reprocessing system 810 to operate and recirculate about 2–5 liters of sterilant. The reprocessing system 810 preferably operates with about 3 liters of sterilant.

In operation, the preferred embodiment of the present invention provides for asynchronous reprocessing of two endoscopes with overlapping cycle time periods. Chemical components for the sterilant are heated and measured as they are moved to and mixed in the reaction chamber 836. The sterilant temperature is monitored and controlled and the reaction of the chemical components in the reaction chamber 836 is timed under the control of a central processor 912. The sterilant's refractive index is measured to ensure the chemical reaction is complete and to verify the presence of the sterilant. Water is added to dilute the sterilant to the use-dilution concentration. Two endoscopes can be reprocessed and sterilized independently and asynchronously using reprocessing bays 816a, 816b. The endoscopes are mounted on the cassettes 880 and connected to the medical device connector 896 through which the lumen of the endoscope will be pressure washed and sterilized. The reprocessing bay doors 846 are secured and the endoscopes are internally and externally washed with soap and water and rinsed. Just prior to the sterilization cycle, the endoscopes are rinsed with hot water to ensure the sterilant will not be cooled upon contact with the endoscopes. The endoscopes are then sterilized internally and externally with sterilant prepared in the reaction chamber 836 just prior to use. The cleaning and sterilization of the endoscope lumen through the medical device connector 896 is assisted by a flow of liquid (soap and water, rinse water, and sterilant in turn) which receives a superimposed pulsating flow of air. This pulsating flow of air causes the liquid flow to become severely unsteady resulting in a scrubbing action on the lumen wall of the endoscope.

Operation of the reprocessing system 810 is monitored by sensors, including those described above, which provide information to the central processor 912. The central processor 912 receives cycle program instructions from a user through the user interface 952. The user interface can be equipped with any form of command signal keys or buttons as is well known in the art. Visual displays of user commands which are entered as well as central processor 912 responses, error messages, status notifications and the like can be presented for the user at the user interface 952. A printer capability can be included to permit the central processor 912 to provide written records of any aspect of reprocessing system operation to the user. Printed records of specific endoscope sterilization can also be printed at the completion of a reprocessing and sterilization cycle. All aspects of the operation of the reprocessing system 810 can be controlled by the central processor 912, to include measuring and mixing of chemical components for the sterilant, metering of water to the reaction chamber 836 for sterilant dilution purposes, washing, rinsing and sterilizing cycles, self-sterilizing, blockage detection and user notification, door ajar sensing and responsive operation termination, and other similar system monitoring and operational controls.

In Operation

In operation, the valves 80, 82 alternate between a first position and a second position as described above causing a first fluid flow path 110 and a second fluid flow path 112. In describing the fluid flow paths 110, 112, downstream is in the flow direction away from the distal end 52 of the umbilical section 28 and towards the distal end 54 of the insertion section 24.

Referring to FIGS. 3, 4, 7, and 8, in the preferred connection to an endoscope, when the device 10 is in the first position 106 causing a first fluid flow path 110, the first valve 80 is open to the fluid supply 84 allowing fluid to flow downstream through the $CO_2$ supply port 40, downstream through the umbilical $CO_2$ channel 22a, downstream through the $CO_2$ cylinder 36, downstream through the control $CO_2$ channel 22b, into the air channel 20, splitting into two flows, the first flow is upstream (first upstream flow) into the control air channel 20b, and the second flow is downstream into the insertion air channel 20c, downstream into the air/water channel 56, through the air/water nozzle 46 and exits the endoscope 12 to a drain 114 at about atmospheric pressure. The first upstream flow continues into the control air channel 20b and flows upstream into the air/water cylinder 32. From the air/water cylinder 32, the fluid splits and flows three ways; a) upstream through the umbilical water channel 16a and out the air/water supply port 42 through the second valve 82 to the drain line 88, b) upstream through the umbilical air channel 20a and out the air/water supply port 42 and air supply port 44 through the second valve 82 and to the drain line 88, and c) downstream through the insertion water channel 16c, downstream through the air/water channel 56, through the air/water nozzle 46 and exits the endoscope 12 to a drain 114 at about atmospheric pressure. The downstream flow through the insertion water channel 16c may flow upstream depending on the relative pressure loss between the various channels.

In a preferred connection to an endoscope, when the device is in the second position 108 causing a second fluid flow path 112, the second valve 82 is open to the fluid supply 84 allowing fluid to flow downstream through the air/water supply port 42 and air supply port 44 and downstream into both the umbilical water channel 16a and the umbilical air channel 20a meeting at the air/water cylinder 32. The fluid splits and flows downstream through control air channel 20b and downstream through the insertion water channel 16c, the flow continues through the insertion water channel 16c and downstream through the air/water channel 56 and through the air/water nozzle 46 and exits the endoscope 12 to a drain 114 at about atmospheric pressure. The flow continues downstream through the control air channel 20b and splits and flows upstream into the $CO_2$ control channel 22b and downstream through the insertion air channel 20c. The flow continues downstream through the insertion air channel 20c through the air/water channel 56 and exits the endoscope 12 to a drain 114 at about atmospheric pressure. The flow continues upstream through the control $CO_2$ channel 22b, upstream through the $CO_2$ cylinder 36, upstream through the umbilical $CO_2$ channel 22a, upstream through the $CO_2$ supply port 40, and through the first valve 80. The fluid flows through the first valve 80 and to the drain line 88.

The second valve 82 may also remain completely closed when the first valve 80 is open to the fluid supply 84. If the second valve 82 remains closed, fluid will not flow as easily or at all from the air/water cylinder 32 through umbilical air channel 20a and umbilical water channel 16a.

Figure 7:
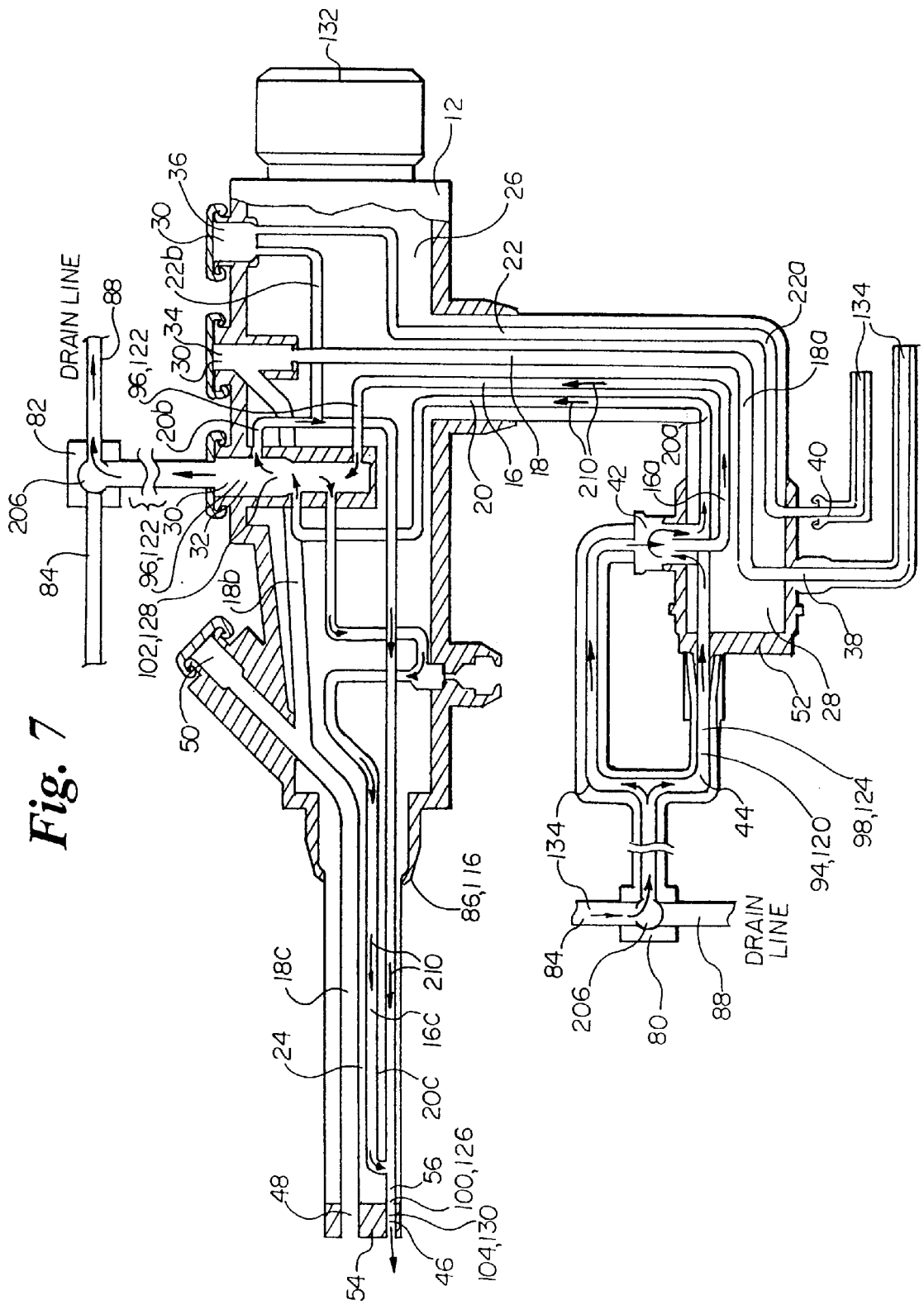
FIG. 7 is a side cross sectional view of an endoscope connected to the device showing an alternate first fluid flow path.

In an alternative connection to an endoscope, as shown in FIG. 7, when the device is in the first position 206 causing a first fluid flow path 210, the first valve 80 is open to the fluid supply 84 allowing fluid to flow downstream through the air/water supply port 42 and air supply port 44 and downstream into both the umbilical water channel 16a and the umbilical air channel 20a meeting at the air/water cylinder 32. In this description of the flow, flow lo through the $CO_2$ channel 22 is not included because the $CO_2$ valve 36 may be closed or there may not be a $CO_2$ channel. The fluid splits and flows three ways; a) downstream through control air channel 20b, b) downstream through the insertion water channel 16c, and c) through the air/water cylinder 32 to the second valve 82. The flow through the control air channel 20b flows downstream through the insertion air channel 20c, through the air/water channel 56 and exits the endoscope 12 to a drain 114 at about atmospheric pressure. The flow through the insertion water channel 16c flows downstream through the air/water channel 56 and through the air/water nozzle 46 and exits the endoscope 12 to a drain 114 at about atmospheric pressure. The flow through the air/water cylinder 32 flows through the second valve 82 and to drain line 88.

Figure 8:
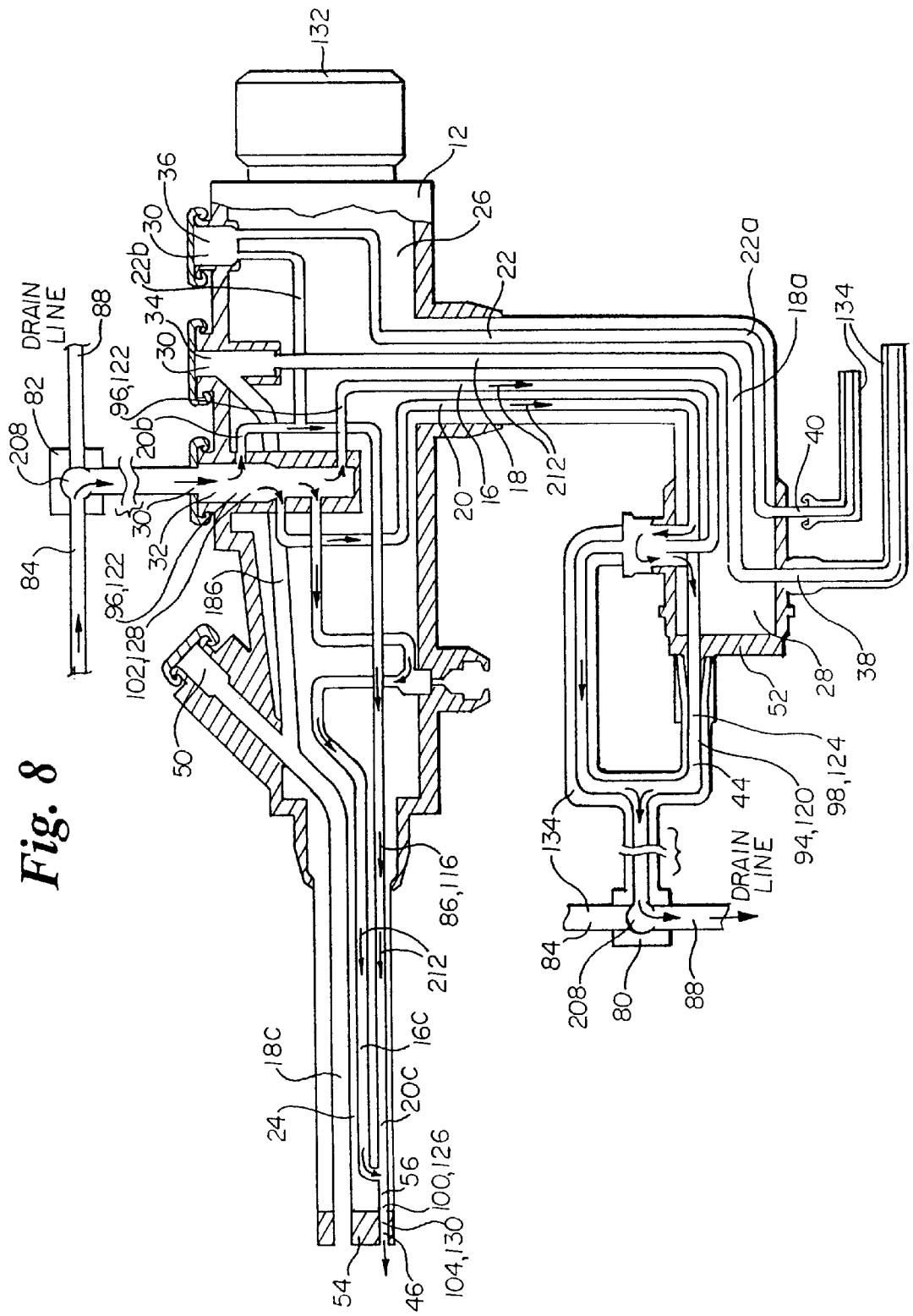
FIG. 8 is a side cross sectional view of an endoscope connected to the device showing an alternate second fluid flow path.
Figure 9A:
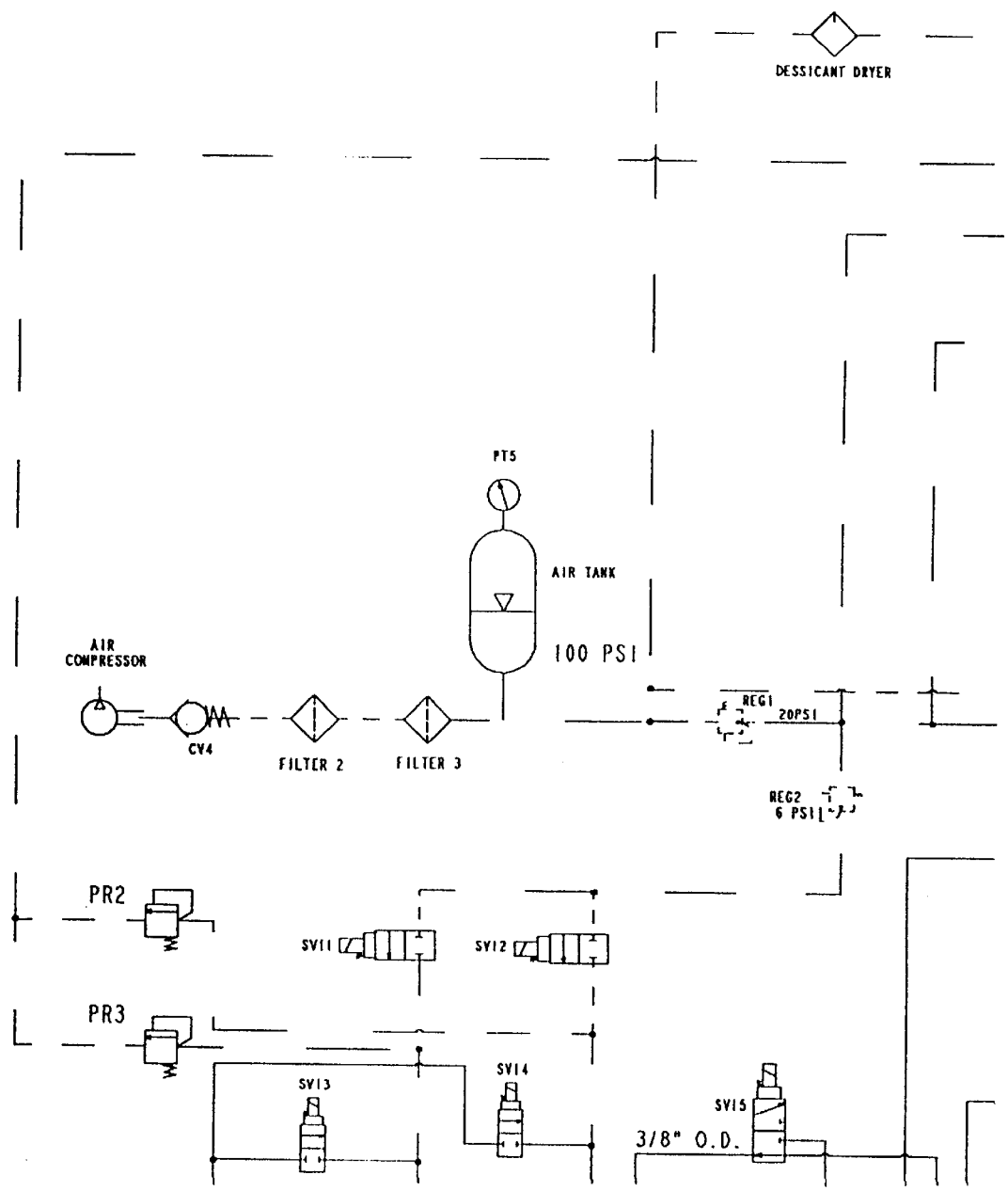
FIG. 9 is a schematic drawing of the device incorporated into an automatic endoscope reprocessing machine controlled by a central processor.
Figure 9B:
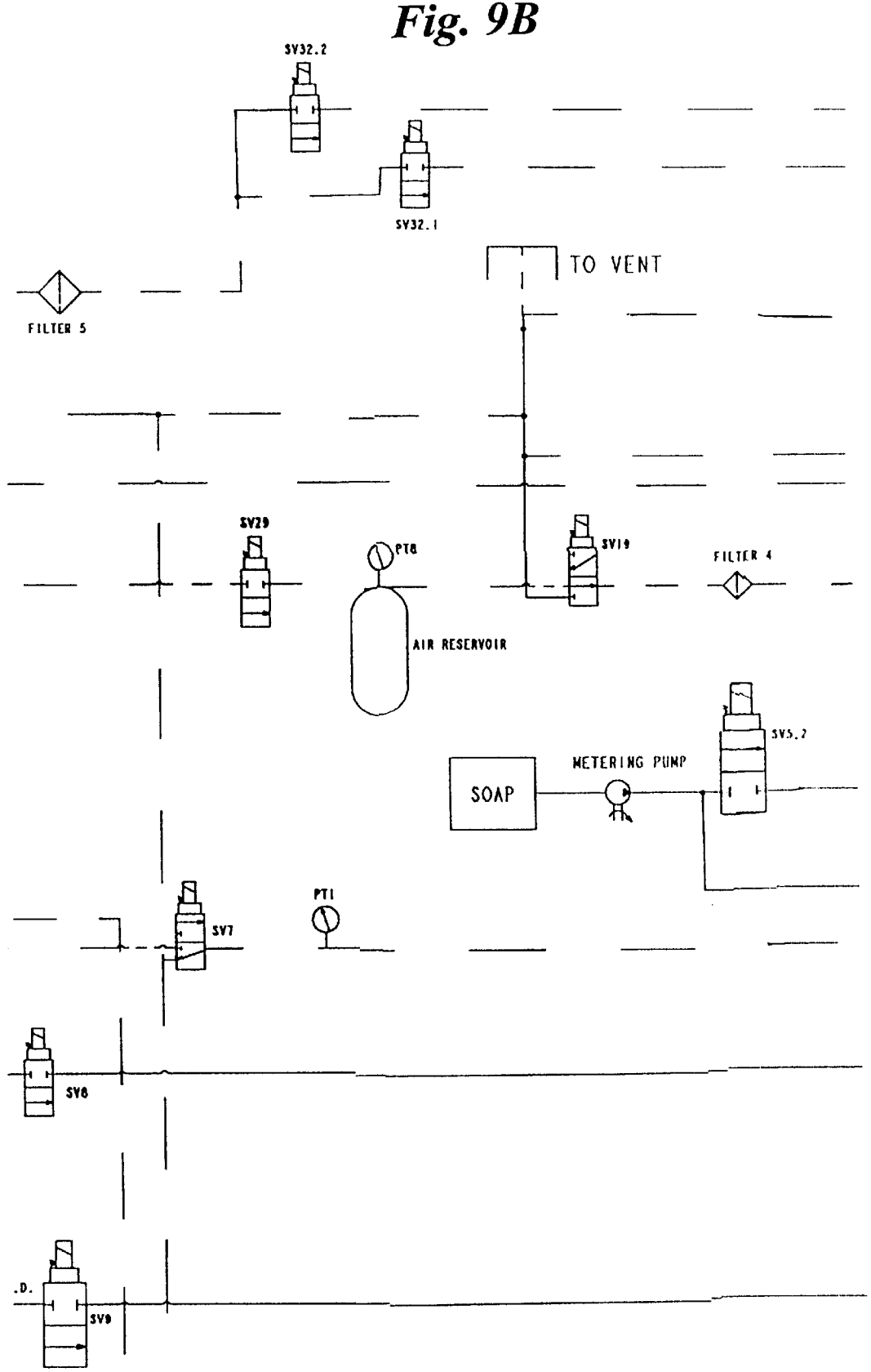
Figure 9C:
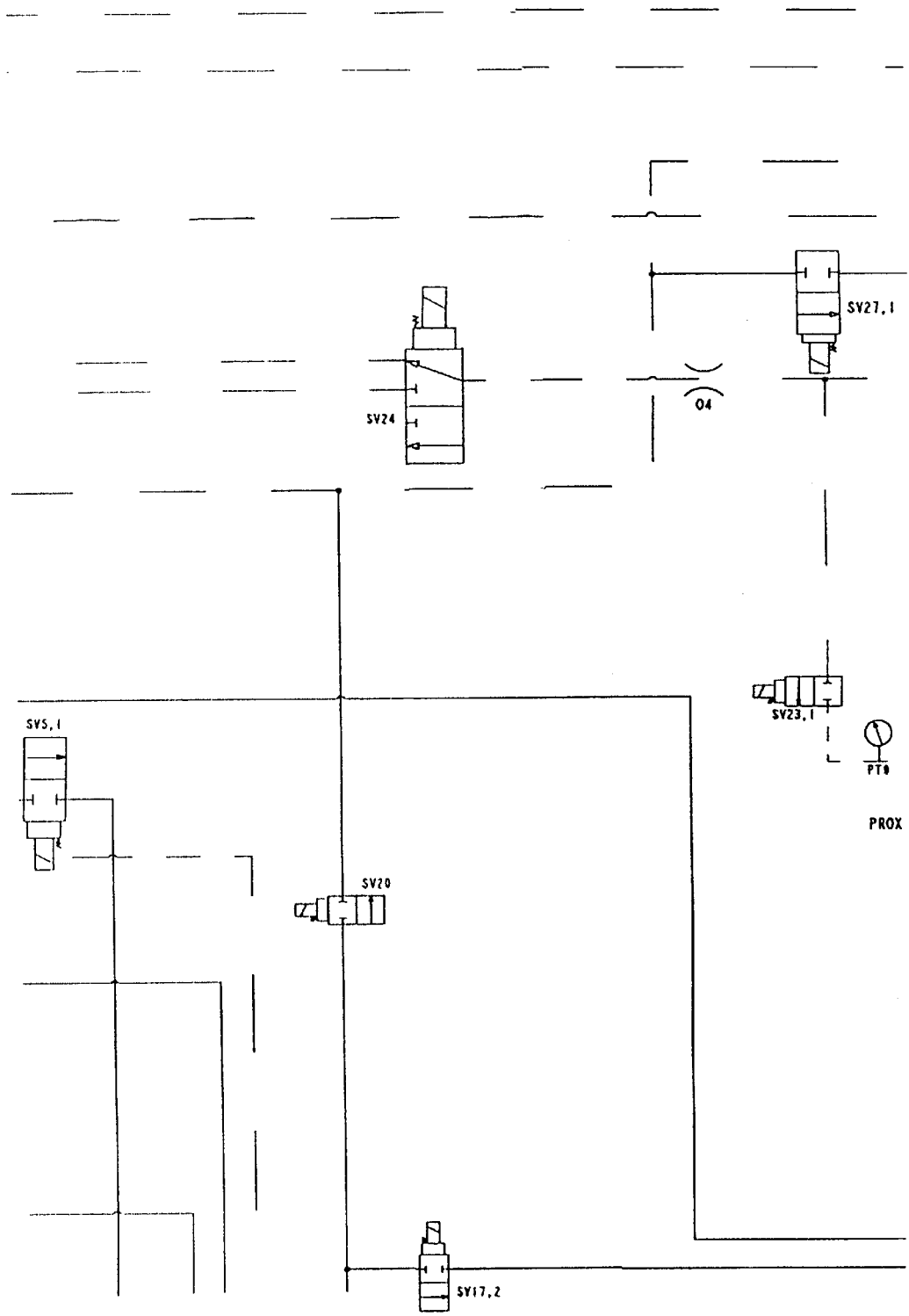
Figure 9D:
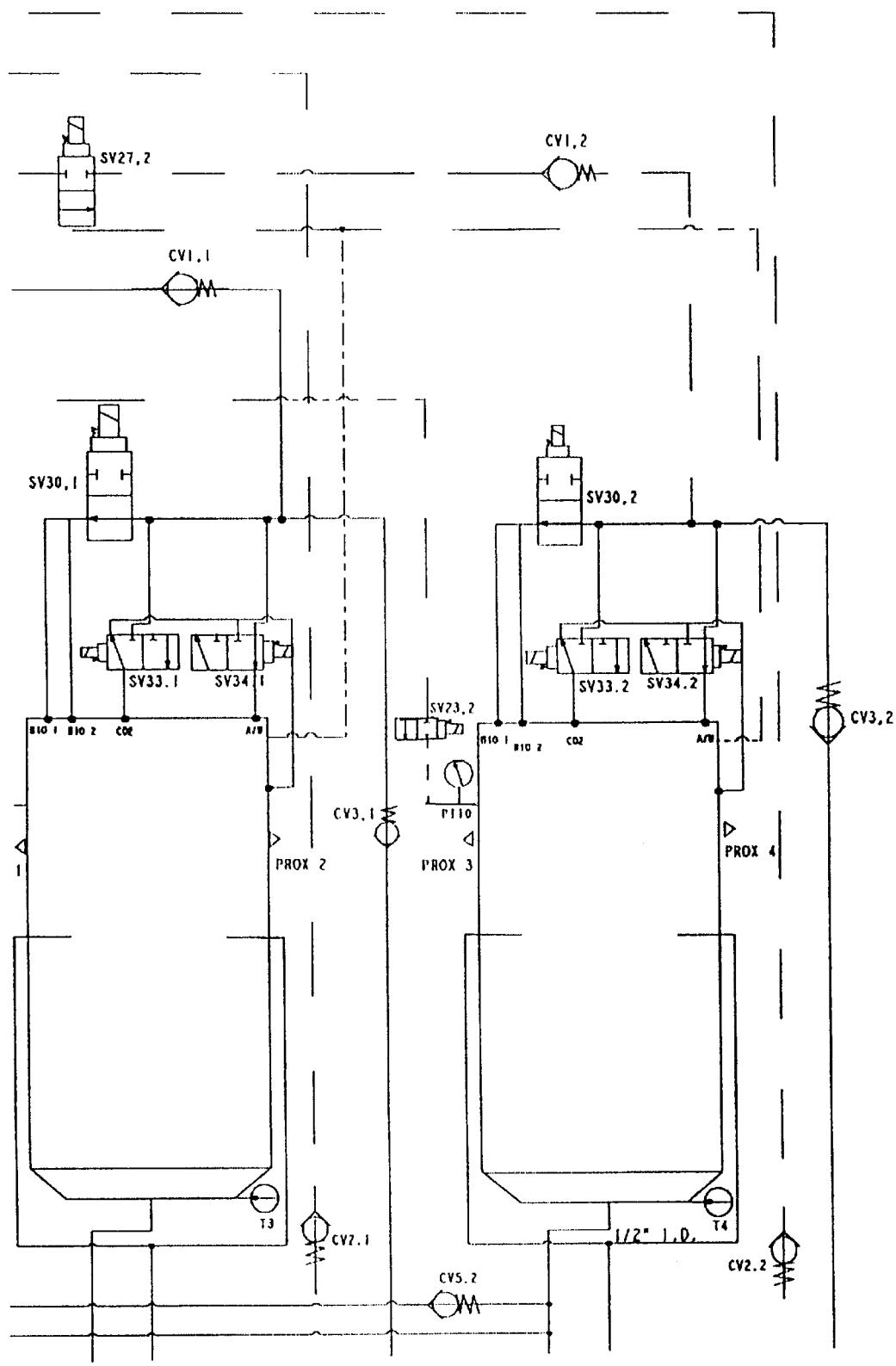
Figure 9E:
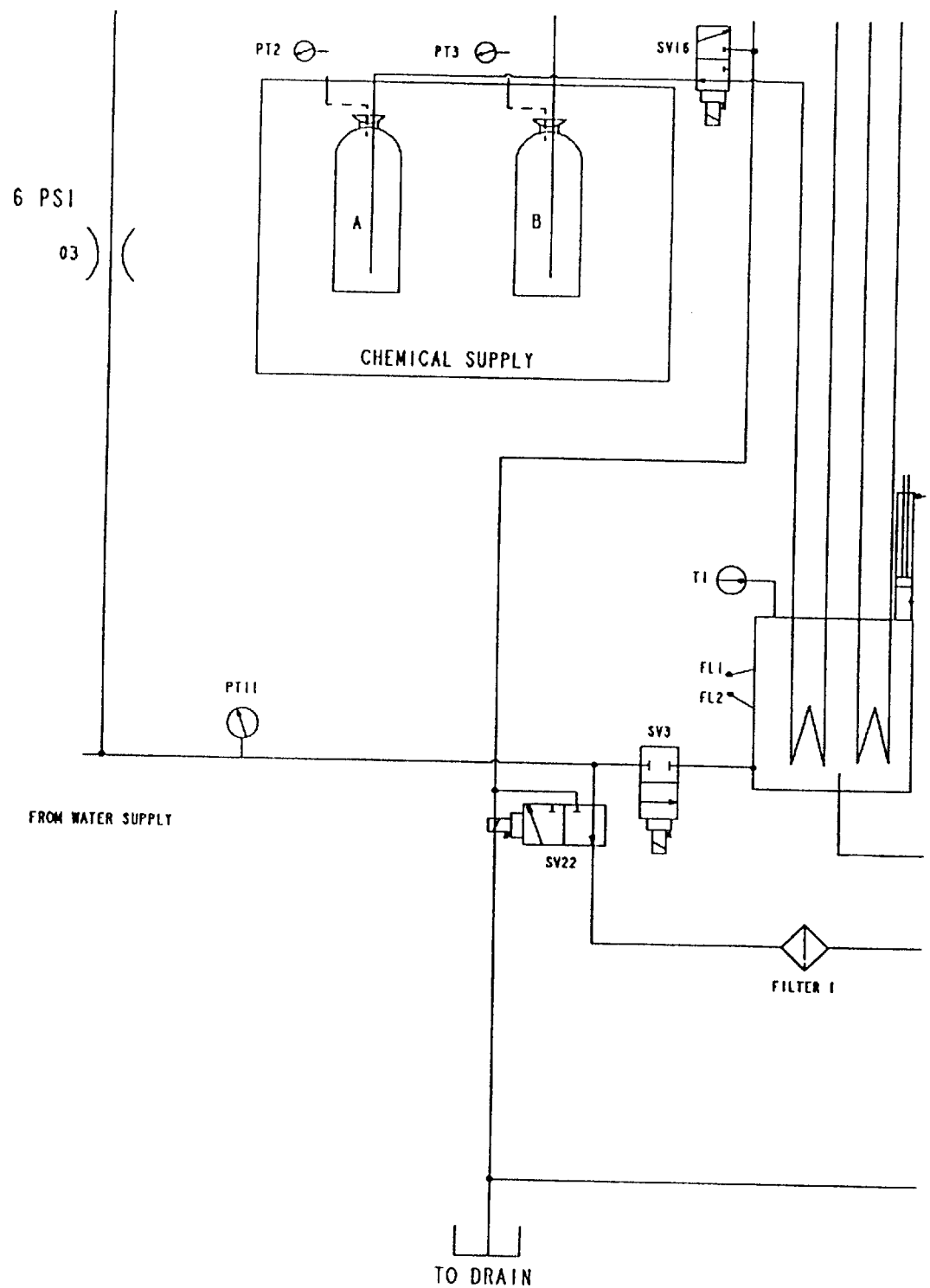
Figure 9F:
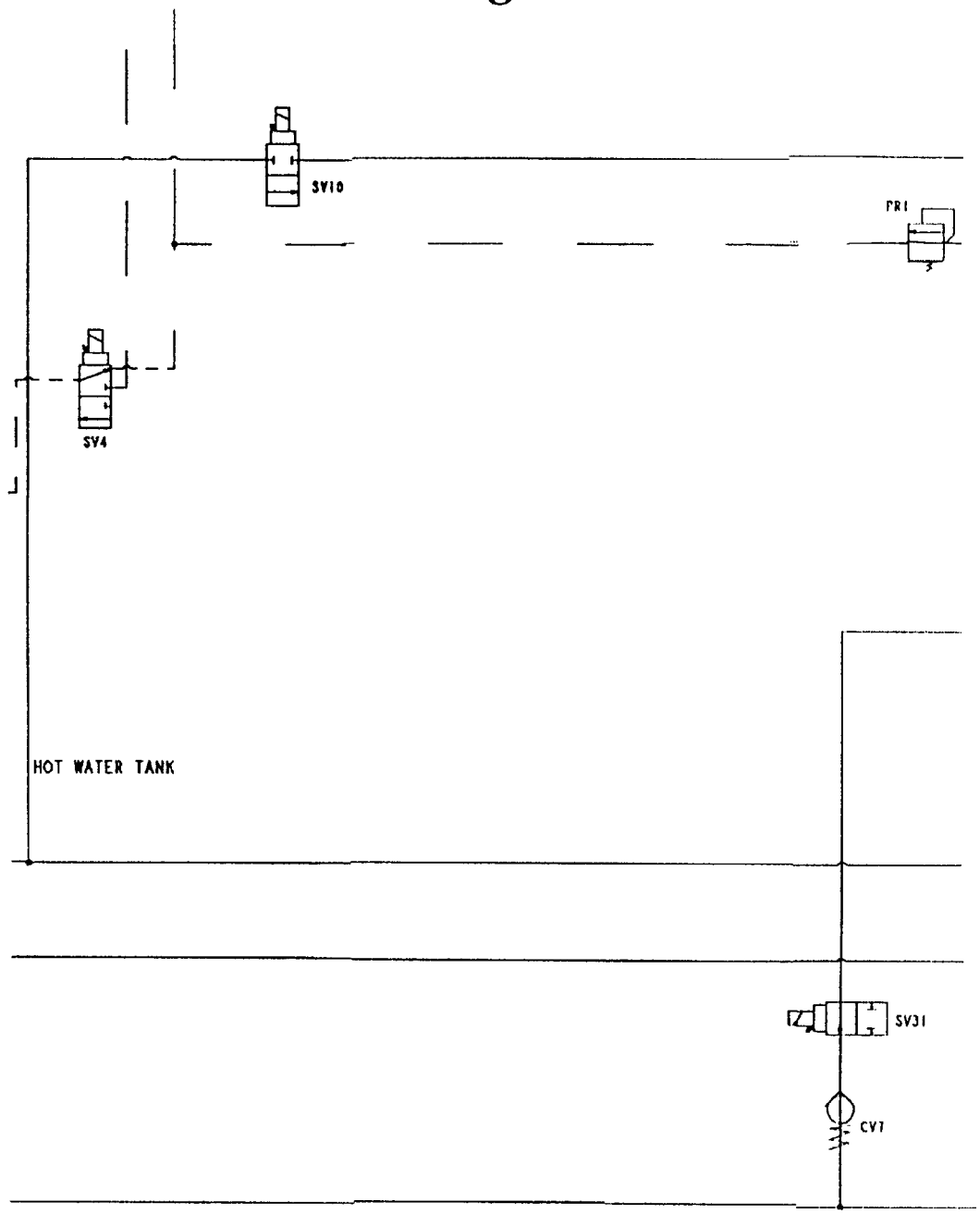
Figure 9G:
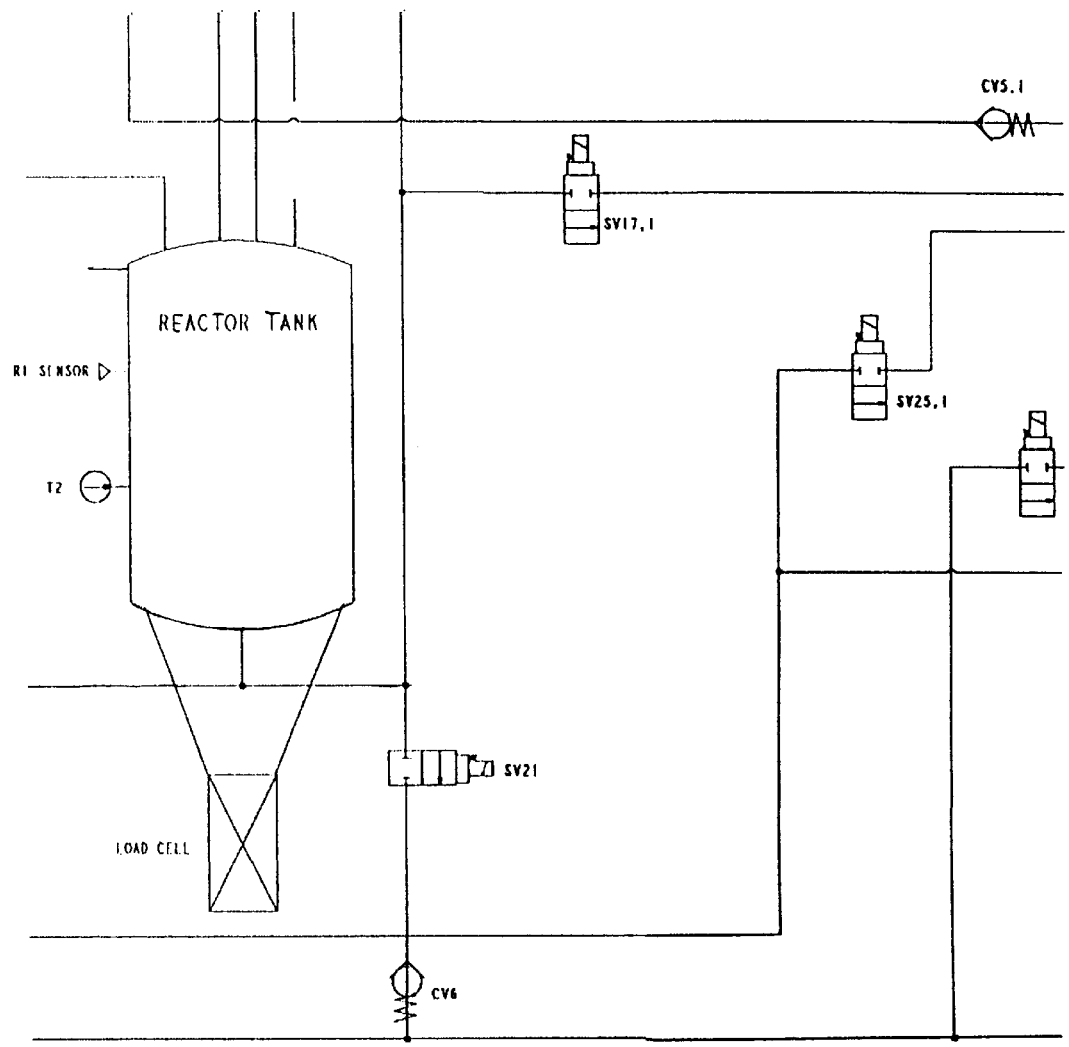
Figure 9H:
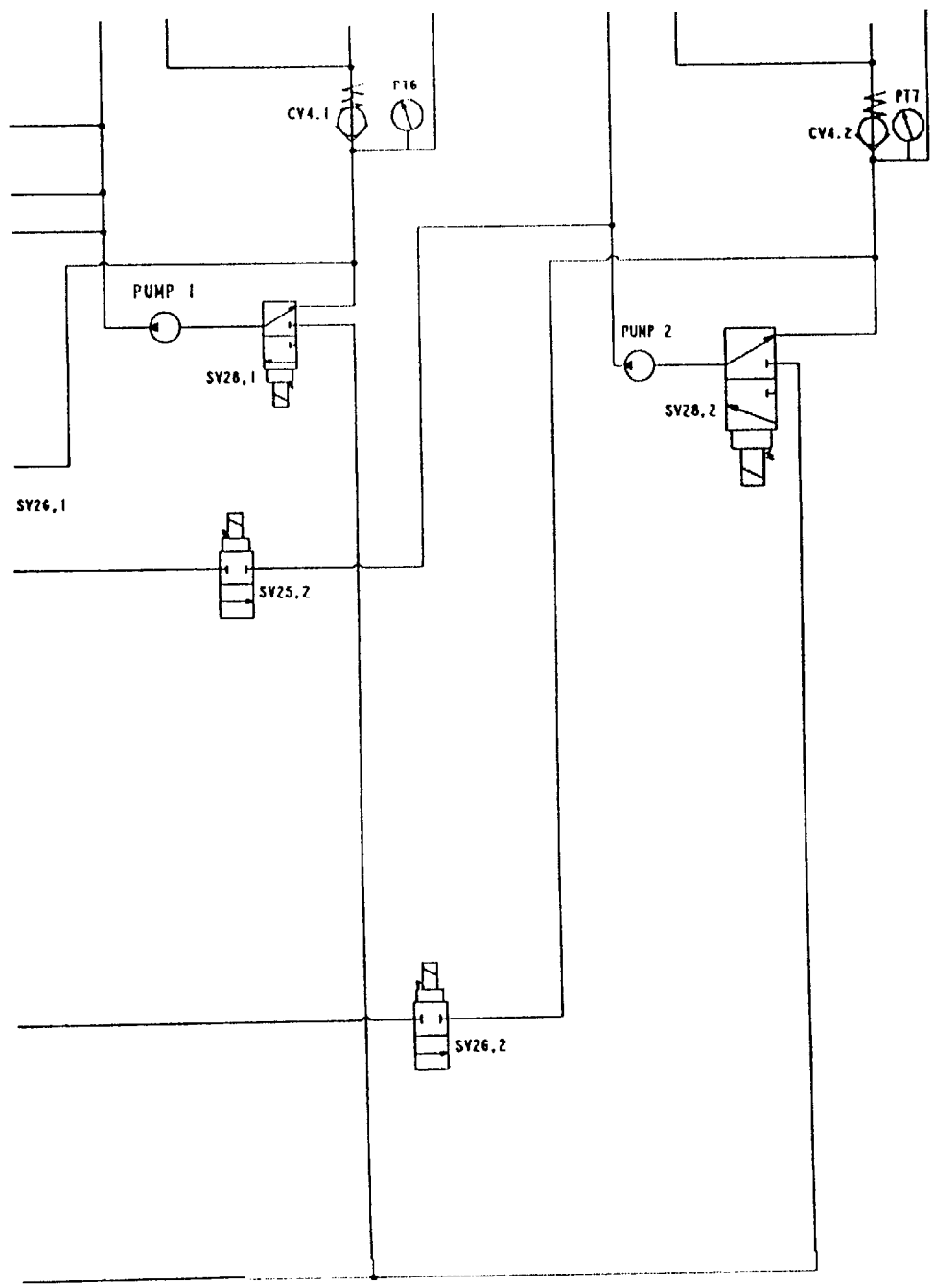
Figure 10A:
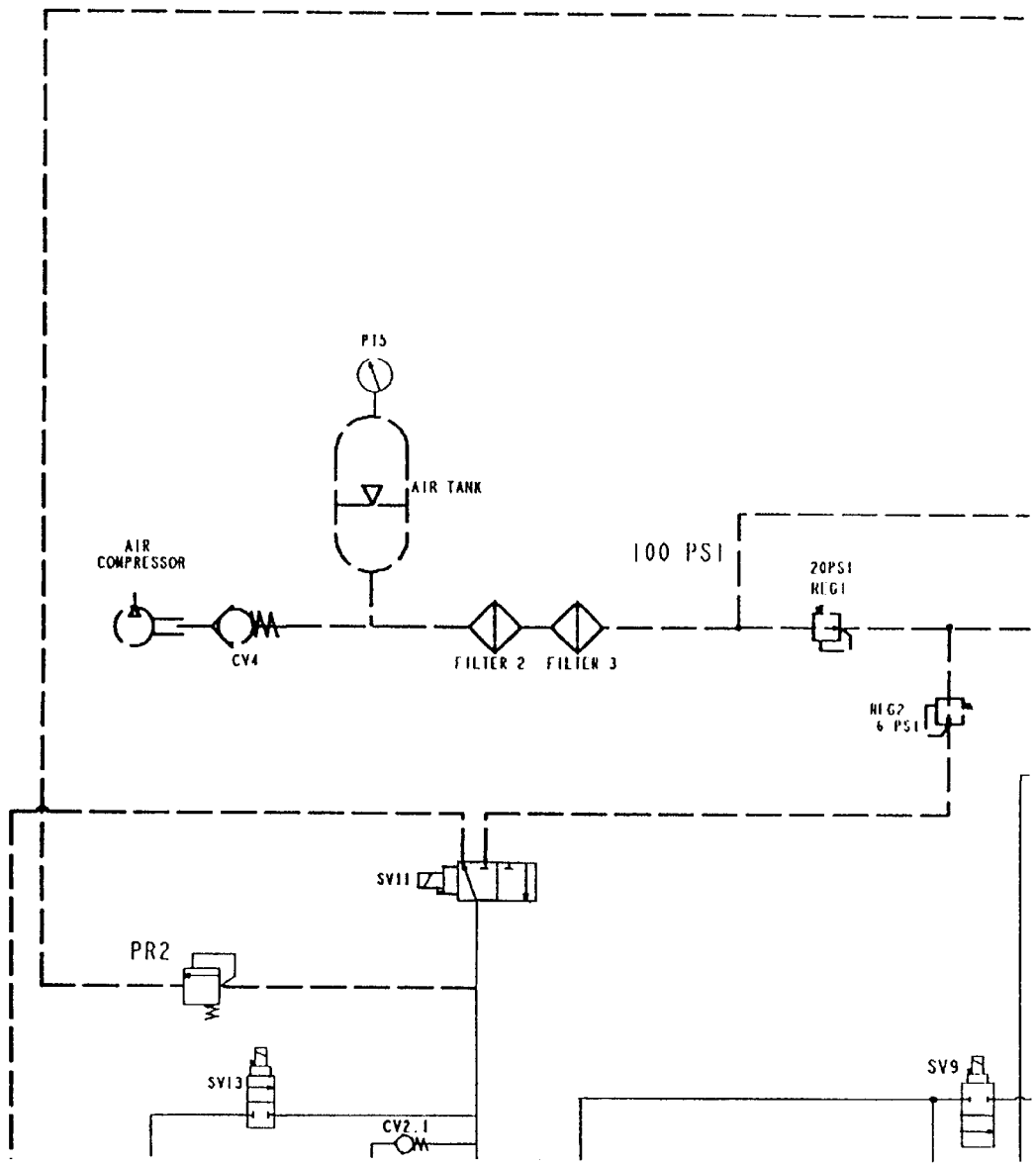
FIG. 10 is a schematic drawing of the device incorporated into an alternate embodiment of an automatic endoscope reprocessing machine controlled by a central processor.
Figure 10B:
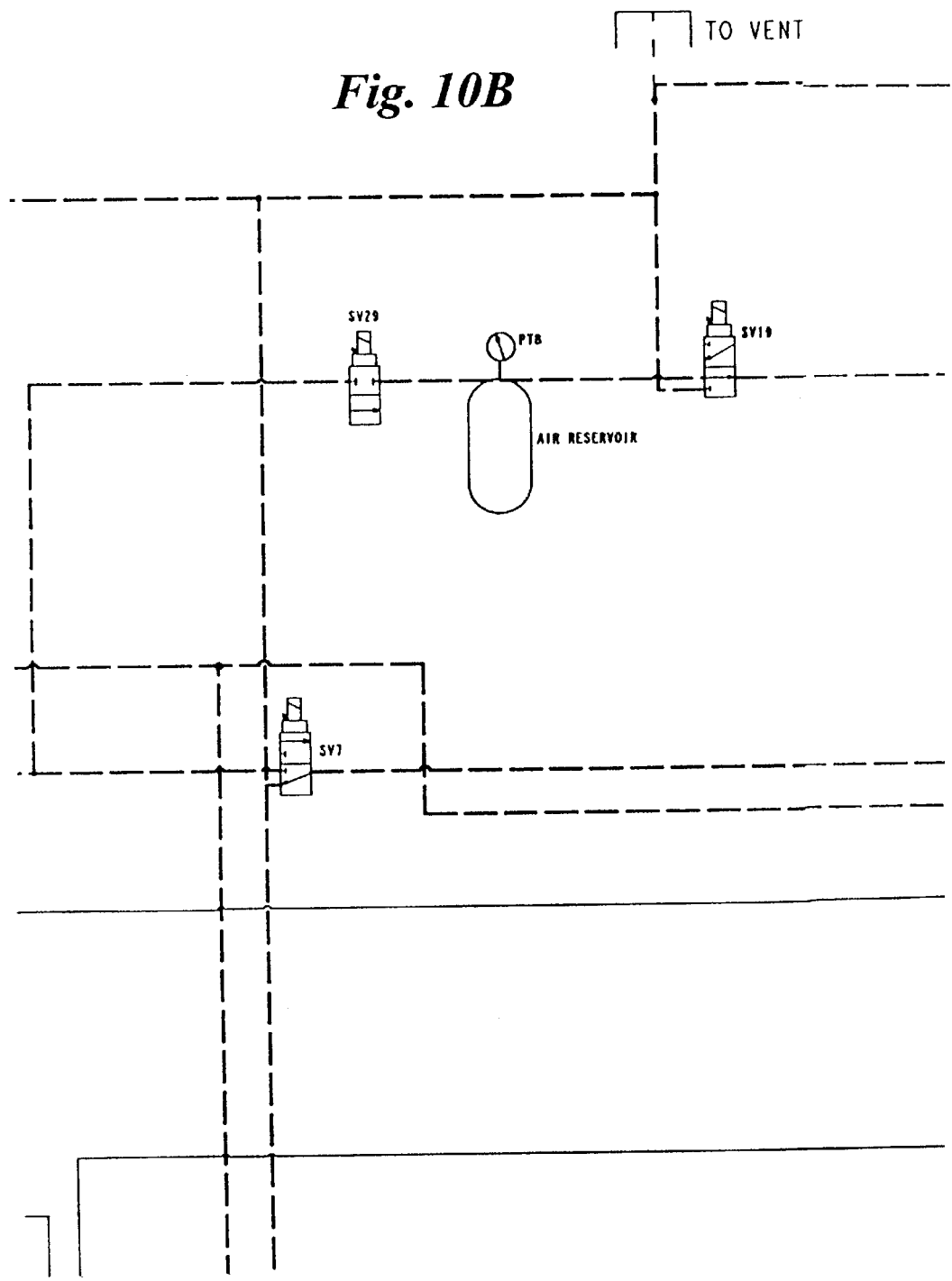
Figure 10C:
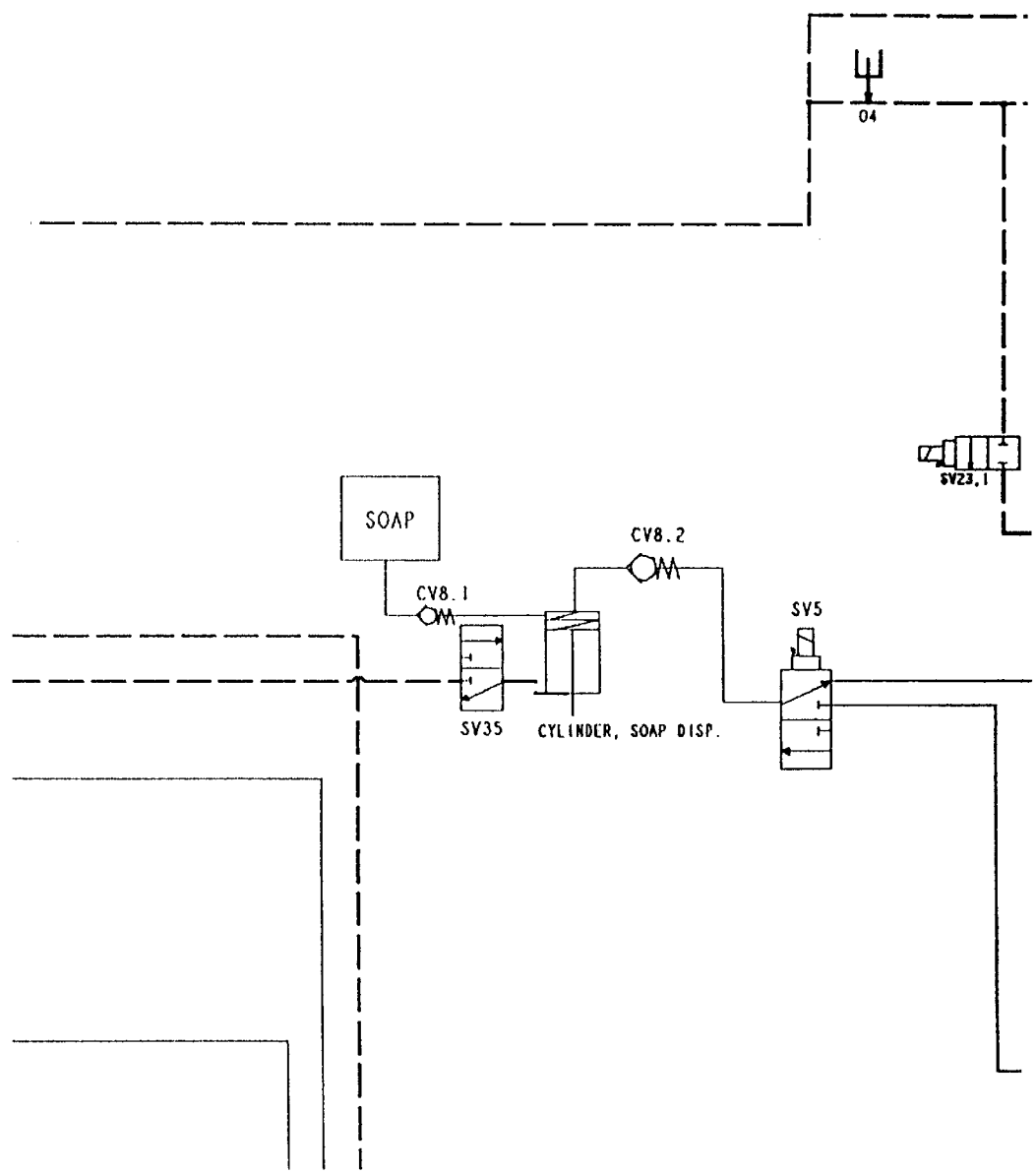
Figure 10D:
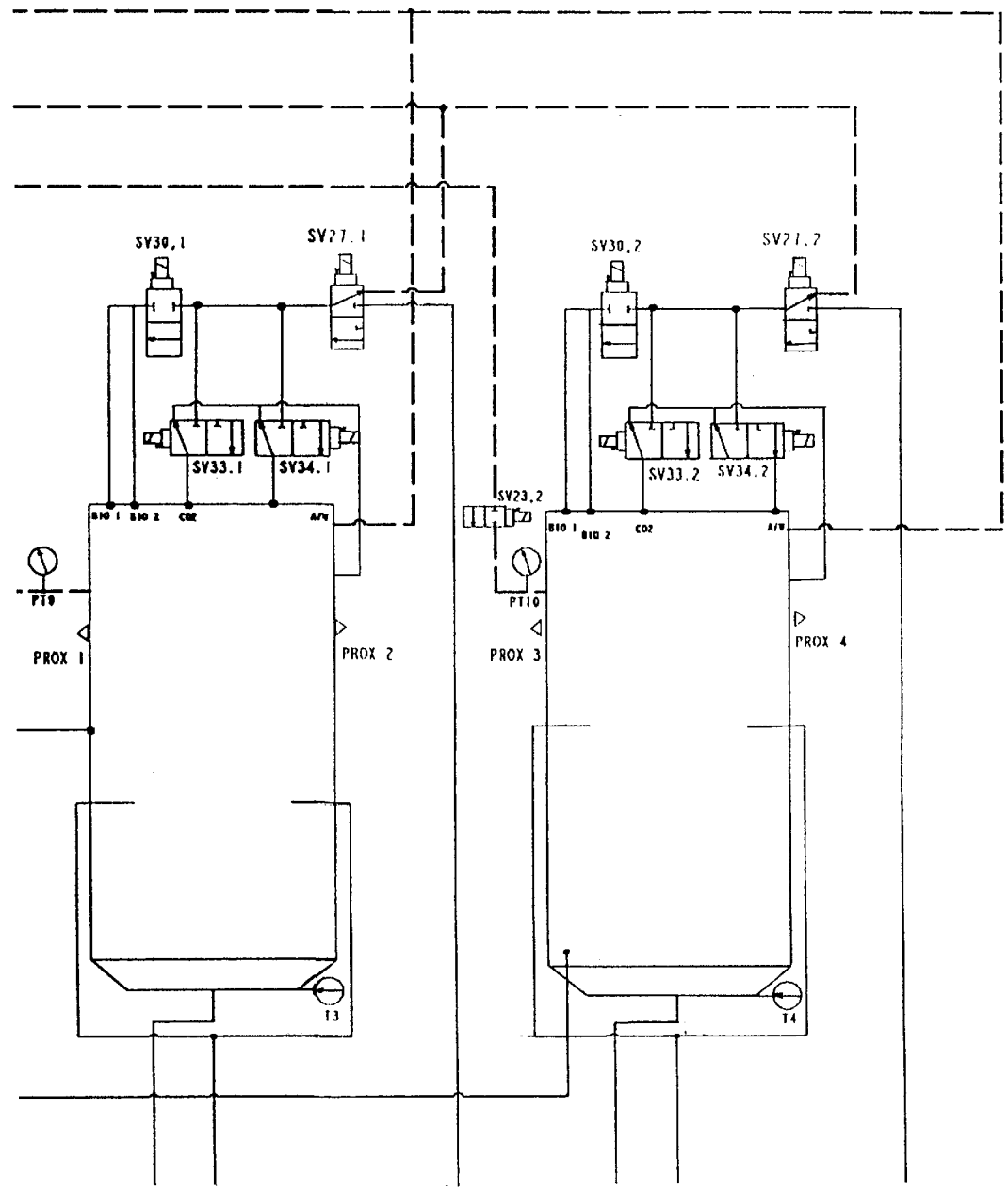
Figure 10E:
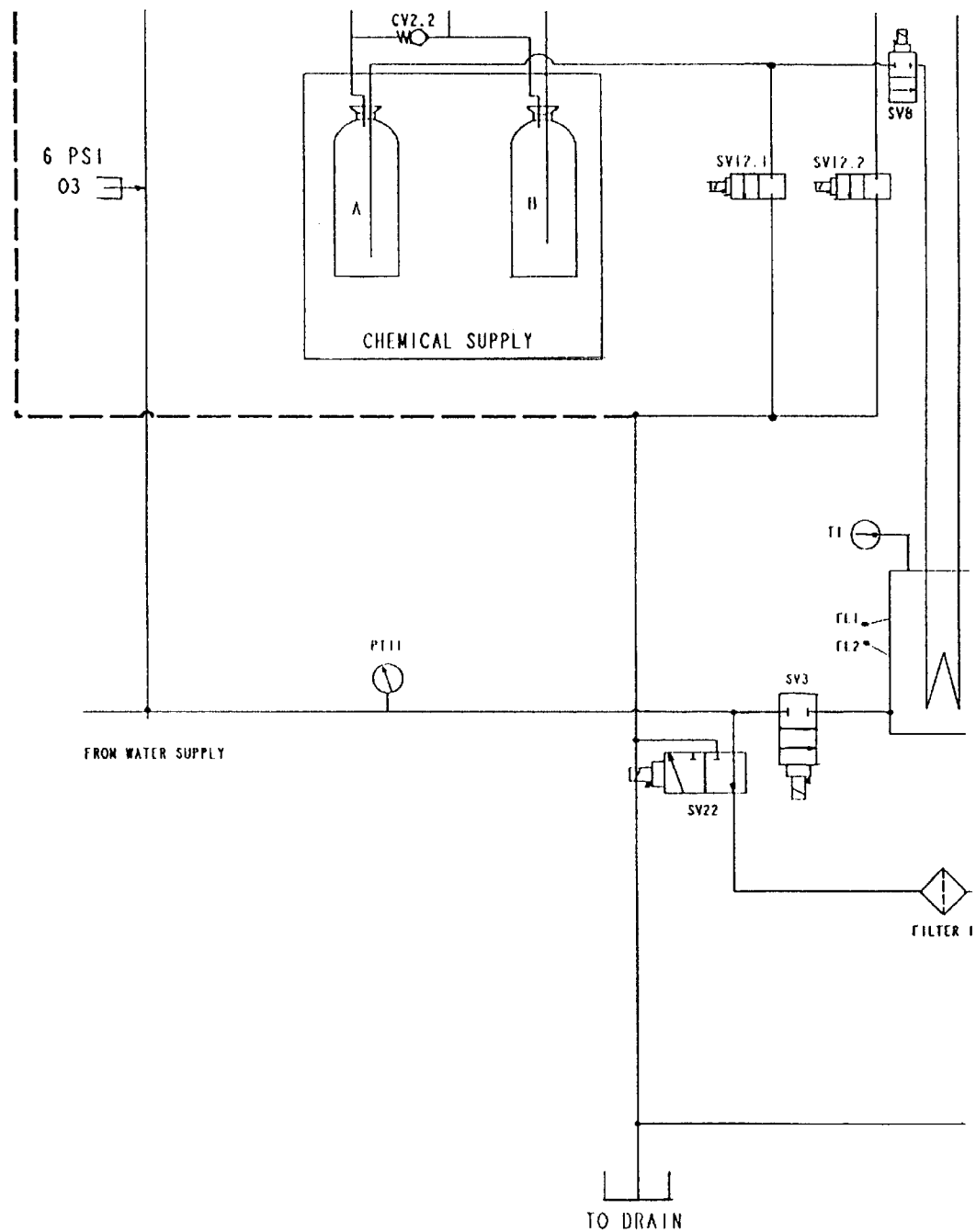
Figure 10F:
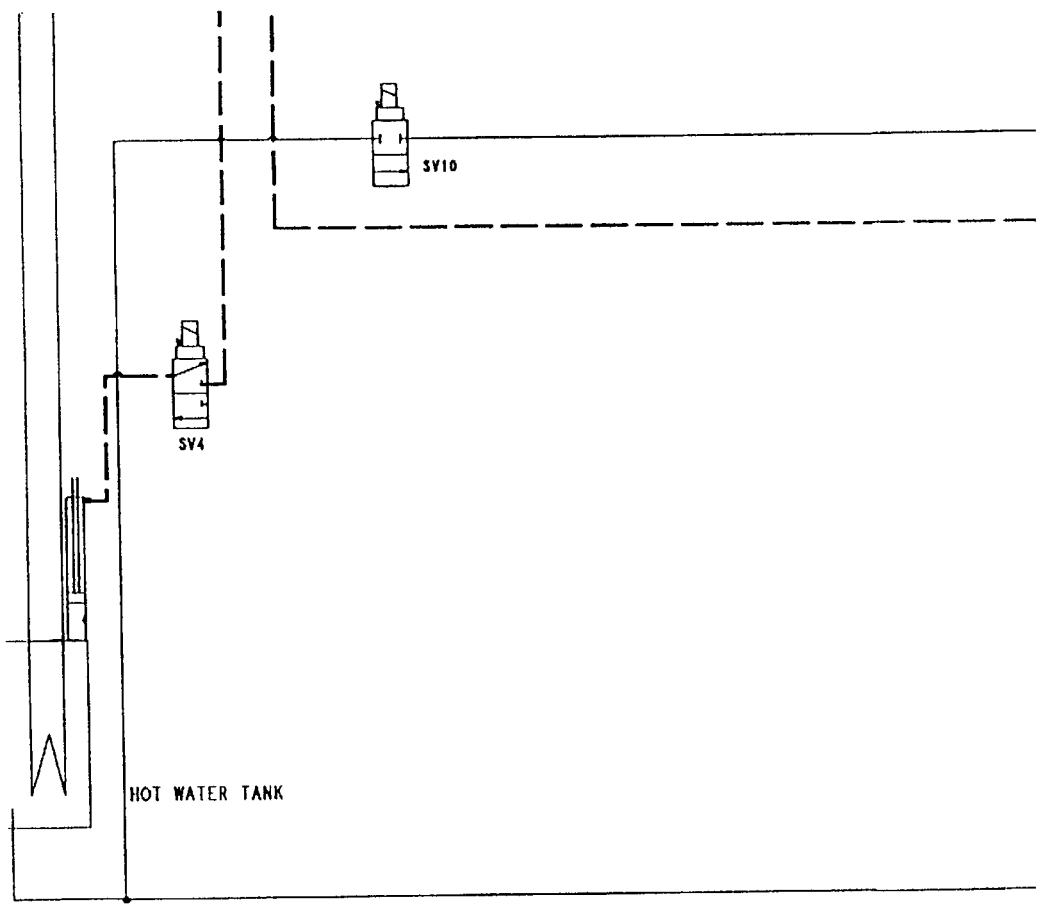
Figure 10G:
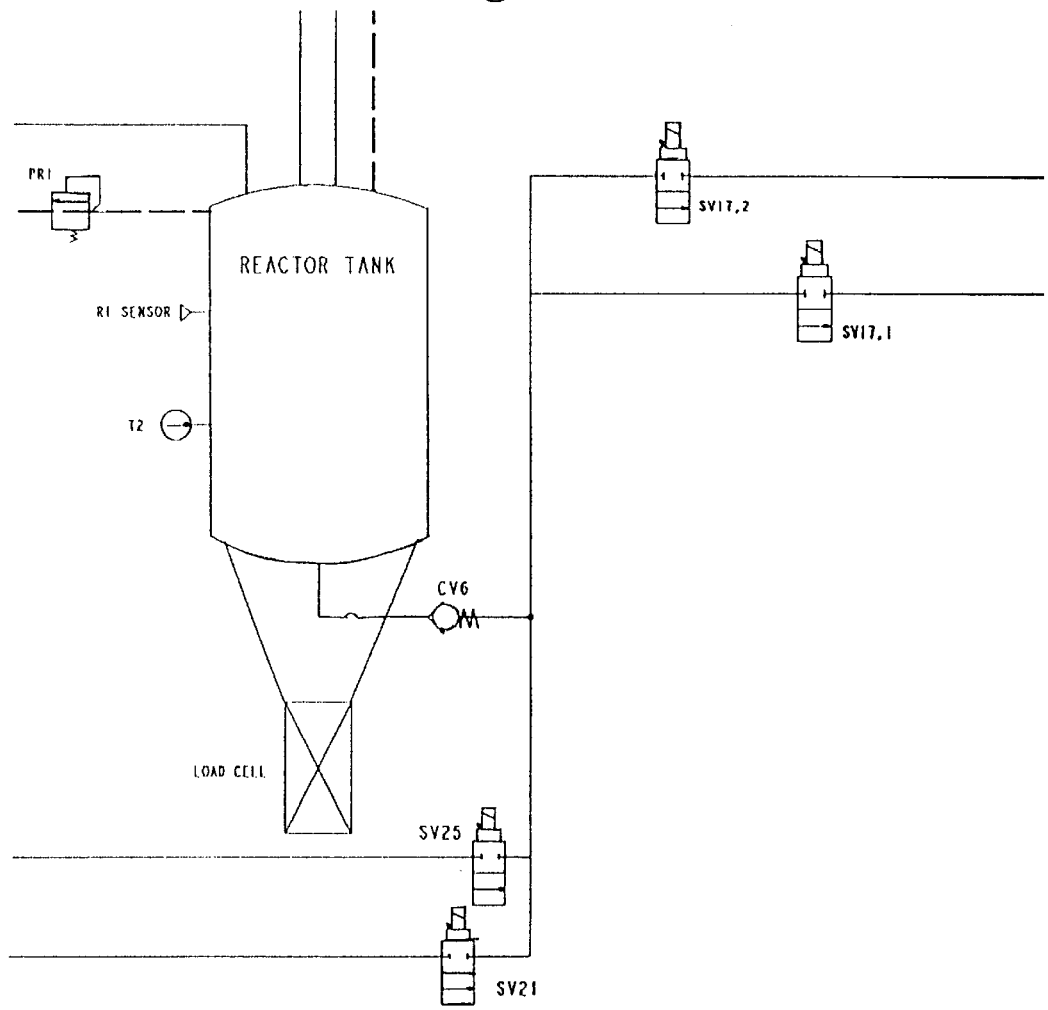
Figure 10H:
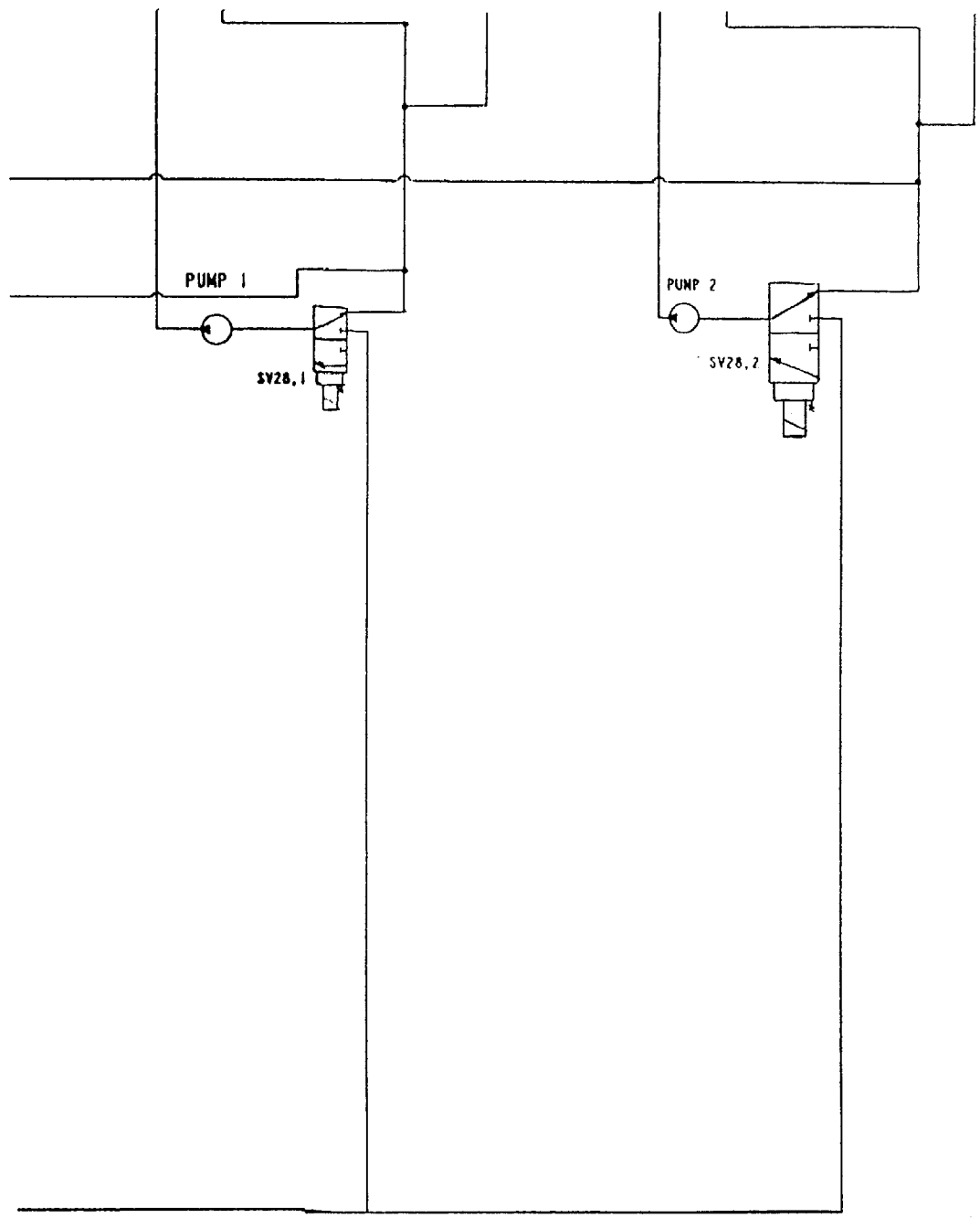

In the alternative connection to an endoscope, as shown in FIG. 8, when the device is in the second position 208 causing a second fluid flow path 212, the second valve 82 is open to the fluid supply 84 allowing fluid to flow downstream through the air/water cylinder 32. In this description of the flow, flow through the $CO_2$ channel 22 is not included because the $CO_2$ valve 36 may be closed or there may not be a $CO_2$ channel. The fluid splits and flows four ways; a) downstream through control air channel 20b, b) downstream through the insertion water channel 16c, and c) upstream into the umbilical water channel 16a, and d) upstream into the umbilical air channel 20a. The flow through the control air channel 20b flows downstream through the insertion air channel 20c, through the air/water channel 56 and exits the endoscope 12 to a drain 114 at about atmospheric pressure. The flow through the insertion water channel 16c flows downstream through the air/water channel 56 and through the air/water nozzle 46 and exits the endoscope 12 to a drain 114 at about atmospheric pressure. The flow upstream into the umbilical water channel 16a flows out the air/water supply port 42 through the first valve 80 and to drain line 88. The flow upstream into the umbilical air channel 20a flows out the air/water supply port 42 and the air supply port 44 through the first valve 80 and to drain line 88.

The suction channel 18 may also be cleaned or sterilized by using the above device 10. The suction channel 18 may be cleaned simultaneously by providing third and fourth valves 90, 92 or separately by connecting to the first and second valves 80, 82. The device 10 may have a third and a fourth position 140, 142, with the third and fourth position respectively the same as the first and second positions except that the third valve 90 replaces the first valve 80 and the fourth valve 92 replaces the second valve 82. The third valve 90 may be connected to the suction supply port 38 and the fourth valve 92 to the biopsy port 50 or alternatively to the suction control valve 34.

With the device in the third position 140 causing a third fluid flow path 136, fluid flows downstream through the suction supply port 38, downstream through the umbilical suction channel 18a, downstream through the suction cylinder 34, downstream through the control suction channel 18b, splitting into a upstream flow through the biopsy port 50 and through the fourth valve 92 to the drain line 88, and a downstream flow through the insertion suction channel 18c and exiting the suction opening 48 of the endoscope 12 to a drain 114 at about atmospheric pressure.

With the device in the fourth position 142 causing a fourth fluid flow path 138, fluid flows downstream through the biopsy port 50, splitting into a downstream flow through the insertion suction channel 18c and exiting through the suction opening 48, and splitting into an upstream flow through the control suction channel 18b, upstream through the suction cylinder 34, upstream through the umbilical suction channel 18a, upstream through the suction supply port 38 through the third valve 90 and to the drain line 88.

Cleaning and Sterilizing Methods

The apparatus and method in accordance with the present invention provides both a method of sterilization of tubular structures, in particular long, narrow, tubular structures, and a method of cleaning the lumens of a medical device.

The sterilization method broadly includes the sterilization of the interior of a tubular structure comprising: a) providing a tubular structure 94, 96, b) providing a sterilizing fluid 116 c) causing the sterilizing fluid 116 to flow at a positive pressure through the tubular structure 94, 96 in a first fluid flow path 110, and d) causing the sterilizing fluid 116 to reverse flow at a positive pressure through the tubular structure 94, 96 in a second fluid flow path 112, so that at least part of the second fluid flow path 112 is opposite as the first fluid flow path 110.

The sterilization method may also include providing the sterilizing fluid 116 at a temperature preferably from about 20 degrees C. to about 50 degrees C. and most preferably about 40 degrees C. to about 50 degrees C. The sterilizing fluid is preferably provided from about 1 minute to about 20 minutes and most preferably for about 10 minutes. The sterilizing method may also provide that the sterilizing fluid 116 provided in the flow and reverse flow method of the present invention has a flow volume from preferably about 100 ml/min to about 1400 ml/min. The flow volume is preferably about 100 ml/min to about 250 ml/min for lumens with a diameter of about 1 mm to about 2 mm and about 600 ml/min to about 1400 ml/min for lumens with a diameter of about 3 mm to about 6 mm. The sterilizing fluid 116 provided in the flow and reverse flow method of the present invention has a flow velocity from preferably about 50 cm/sec to about 500 cm/sec and most preferably about 50 cm/sec to about 250 cm/sec. The sterilizing fluid 116 provided in the flow and reverse flow has a pressure preferably below about 20 psi and most preferably about 10 psi to about 20 psi.

The sterilization method may also include wherein the tubular structure 94, 96 has a diameter of less than about 6 mm.

The sterilization method may also include starting the first fluid flow path 110 and the second fluid flow path 112 in one end of a medical device.

The sterilization method may also include starting one fluid flow path 210, 212 in the control head or other central attachment point of a medical device.

The sterilization method may also include providing the device 10 of the present invention.

The sterilization method may also include controlling the flow and said reverse flow by a central processor.

The present invention also includes a method of cleaning a medical device with lumens 14. The cleaning method broadly includes a method of cleaning the lumens 14 of a medical device including a) providing a medical device with a first lumen 120 and a second lumen 122, each lumen 120, 122 having a proximal end 124, 128 and a distal end 126, 130 and the distal end 126, 130 of at least one of the lumens 120,122 is open to a drain 114 at about atmospheric pressure; b) providing a cleaning fluid 86; c) causing the cleaning fluid 86 to flow through the lumens 120,122 in a first fluid flow path 110 starting at the proximal end 124 of the first lumen 120; and d) causing the cleaning fluid 86 to reverse flow through the lumens 120, 122 in a second fluid flow path 112 starting at the proximal end 128 of the second lumen 122, wherein at least part of the second fluid flow path 112 is opposite the first fluid flow path 110.

The cleaning method may also include providing a medical device with the proximal end 124, 128 of each lumen 120, 122 located in one end of the medical device.

The cleaning method may also include starting one fluid flow path 210, 212 in the control head or other central attachment point of a medical device.

The cleaning method may also include providing the device 10 of the present invention.

The cleaning method may also include draining the first fluid flow path 110 through the proximal end 128 of the second lumen 122 and draining the second fluid flow path 112 through the proximal end 124 of the first lumen 120.

The cleaning method may also provide that the cleaning fluid 86 provided in the flow and reverse flow has a flow volume from preferably about 100 ml/min to about 1400 ml/min. The flow volume is preferably about 100 ml/min to about 250 ml/min for lumens with a diameter of about 1 mm to about 2 mm and about 600 ml/min to about 1400 ml/min for lumens with a diameter of about 3 mm to about 6 mm. The cleaning fluid 86 provided in the flow and reverse flow has a flow velocity from preferably about 50 cm/sec to about 500 cm/sec and most preferably from about 50 cm/sec to about 250 cm/sec. The cleaning fluid 86 provided in the flowing and reverse flowing has a pressure preferably below about 20 psi and most preferably from about 10 psi to about 20 psi.

The cleaning method may also include providing the device 10 of the present invention.

The cleaning method may also provide controlling the flow and the reverse flow by a central processor.

The present device and method also improves sterilization of endoscopes. As shown in the following examples, complete sterilization of the lumens of endoscopes can be difficult, in particular, the $CO_2$ lumen of the endoscope. The $CO_2$ lumen typically has bends, connections, restrictions, and irregularities making it difficult to provide complete cleaning or sterilization of the $CO_2$ lumen.

The following tests show that the device and method of the present invention provides an unexpected improvement in the sterilization of the endoscope.

For the following experiments, the endoscope was coiled loosely and attached to a rack, which held it vertically. The control head was mounted so that the eyepiece was up and the control knobs were vertical. The suction, air/water, and $CO_2$ channels were inoculated with a total of $1-8 \times 10^6$ spores and dried for an hour. The endoscope was treated with a performic acid based sterilant in a device that pumped sterilant through the channels and sprayed the exterior of the endoscope with sterilant. The endoscope was rinsed briefly and assayed for surviving organisms. If even one survivor was found, the endoscope was judged nonsterile. As shown in the table below, a large number of variables were tested in our efforts to sterilize endoscopes consistently. The best results seemed to be obtained when the pressure (flow rate) in the lumens was increased to 20 psi, close to the maximum allowed. We noted that survivors were rarely found in the suction channel, the largest, least complex channel. Survivors were frequently found in the $CO_2$ channel, which has a small lumen and an intricate, constricted valve construction. Flowing sterilant in both directions unexpectedly consistently eliminated all of the survivors in the endoscopes including in the $CO_2$ channel. As shown in the table, this procedure gave consistent sterilization even with a reduced pressure of 12 psi in the lumens.

TABLE I

Sterilizing endoscopes with performic acid based sterilant, 10 minutes at 40–45° C.

| Connection point | Variable | Number scopes sterile/total tested |
|---|---|---|
| Control head | 4 psi pressure in lumens | 0/3 |
| | 10 psi pressure in lumens | 1/2 |
| | 20 psi pressure in lumens | 3/4 |
| Light guide | 4 psi pressure in lumens | 0/3 |
| | 10 psi pressure in lumens | 0/5 |
| | 20 psi pressure in lumens | 5/8 |

TABLE I-continued

Sterilizing endoscopes with performic acid based sterilant, 10 minutes at 40–45° C.

| Connection point | Variable | Number scopes sterile/total tested |
|---|---|---|
| Control head or light guide | Scope orientation - - lay flat | 2/4 |
| Control head | Scope orientation -- control knobs horizontal | 0/2 |
| | Scope orientation -- control head upside down | 0/2 |
| Light guide | Increase sterilant volume three-fold | 1/3 |
| | Prewarm scope to 45° C. | 1/2 |
| Control head | Use restrictors to channel more flow to $CO_2$ channel | 2/7 |
| Light guide | Connect to air/water only, flow to $CO_2$ channel from control head | 2/8 |
| Control head or light guide | Interrupt sterilant flow with periodic air pulses | 1/5 |
| Light guide | Reverse flow in the $CO_2$ channel | 10/10 |

TABLE II

DETAILED DATA TABLE:
Improved Application of Liquids to Lumens by Reverse Flow
Sterilization of endoscopes on an automatic endoscope reprocessor, 40–45° C, 15% performic acid based sterilant in RO water, 10-minute exposure.

| Conn[f] | Chann press | Other | Number of survivors[k] | | | | | | | |
| | | | Suct[a] | $CO_2$[b] | ACI[j] | Ext | A/W port | $CO_2$ valve | Suct Port | A/W port LG |
|---|---|---|---|---|---|---|---|---|---|---|
| CH | | Connectors attached before inoculation, foamy, airpulse during sterilization (performic acid based sterilant without phosphoric) | 0 | 0 | 0 | 0 | 0 | 0 | 0 | 0 |
| | | | 1 | 0 | 0 | 0 | 0 | 0 | 0 | 0 |
| CH | | Foamy, no airpulse | 0 | 0 | 1 | 0 | 0 | 0 | 0 | 0 |
| LG | | Leaking plugs (modified ACI) at CH, foamy, performic acid based sterilant plus phosphoric acid | 32 | TNTC | TNTC | 0 | 0 | 7 | 0 | 0 |
| | | | 2 | 66 | 8 | 0 | 0 | 0 | 0 | 0 |
| | | | 0 | 0 | 0 | 0 | 0 | 0 | 0 | 0 |

TABLE II-continued

DETAILED DATA TABLE:
Improved Application of Liquids to Lumens by Reverse Flow
Sterilization of endoscopes on an automatic endoscope
reprocessor, 40–45° C, 15% performic acid based
sterilant in RO water, 10-minute exposure.

| | | | \multicolumn{8}{c}{Number of survivors[k]} | | | | | | | |
|---|---|---|---|---|---|---|---|---|---|---|
| Conn[f] | Chann press | Other | Suct[a] | $CO_2$[b] | ACI[j] | Ext | A/W port | $CO_2$ valve | Suct Port | A/W port LG |
| CH | 10 psi | 12 L sterilant, lay scopes flat | 0 | 0 | 0 | 0 | 0 | 0 | 0 | 0 |
| | | | 0 | 0 | 0 | 0 | 0 | 0 | 0 | 0 |
| CH | 4 psi | Low foam by low pump speed (400 rpm) | 0 | 0 | 1 | 0 | 0 | 0 | 0 | 0 |
| | | | 0 | 3 | 2 | 0 | 0 | 0 | 0 | 0 |
| | | | 0 | 2 | 0 | 0 | 0 | 0 | 0 | 0 |
| LG | 4 psi | Low foam | 0 | 0 | 7 | 0 | 0 | 0 | 0 | 0 |
| | | | 0 | 1 | 0 | 0 | 0 | 0 | 0 | 0 |
| | | | 0 | 12 | 4 | 0 | 0 | 0 | 0 | 0 |
| CH | 10 psi | Standard position, raise channel pressure by restricting flow to spray arms (from this point forward) | 0 | 0 | 0 | 0 | 0 | 0 | 0 | 0 |
| | | | 0 | 1 | 1 | 0 | 0 | 0 | 0 | 0 |
| | | Knobs up on control head | 1 | 111 | 0 | 0 | 0 | 0 | 0 | 0 |
| | | | 0 | 1 | 0 | 0 | 0 | 0 | 0 | 0 |
| | | Upside down | 0 | 38 | 17 | 0 | 0 | 0 | 0 | 0 |
| | | | 2 | 7 | 0 | 0 | 0 | 0 | 0 | 0 |
| LG | 10 psi | | 0 | 13 | 9 | 0 | 0 | 0 | 0 | 0 |
| | | | 0 | 2 | 0 | 0 | 0 | 0 | 0 | 0 |
| LG | 18–20 psi | | 0 | 0 | 0 | 0 | 0 | 0 | 0 | 0 |
| | | | 0 | 0 | 0 | 0 | 0 | 0 | 0 | 0 |
| | | | 0 | 0 | 0 | 0 | 0 | 0 | 0 | 0 |
| | | | 0 | 0 | 0 | 0 | 0 | 0 | 0 | 0 |
| | | | 0 | 0 | 0 | 0 | 0 | 0 | 0 | 0 |
| | | | 0 | 3 | 4 | 0 | 0 | 0 | 0 | 0 |
| | | | 0 | 1 | 0 | 0 | 0 | 0 | 0 | 0 |
| | | | 0 | 23 | 4 | 0 | 0 | 0 | 0 | 0 |
| LG | 18–20 psi | 12 L sterilant | 0 | 0 | 0 | 0 | 0 | 5 | 0 | 0 |
| | | | 0 | 0 | 0 | 0 | 0 | 0 | 0 | ND |
| | | | 1 | 0 | 0 | 0 | 0 | 0 | 0 | 0 |
| LG | 18–20 | Dry at 45° C. | 2 | TCTN | TNTC | 0 | 0 | 0 | 0 | 0 |
| | | | 0 | 0 | 0 | 0 | 0 | 0 | 0 | 0 |
| CH | 18–20 | | 0 | 0 | 0 | 0 | 0 | 0 | 0 | 0 |
| | | | 0 | 0 | 0 | 0 | 0 | 0 | 0 | 0 |
| | | | 0 | 0 | 0 | 0 | 0 | 0 | 0 | 0 |
| | | | 0 | 0 | 6 | 0 | 0 | 0 | 0 | 0 |
| CH | 18–20 | Add restrictor to A/W connector on light guide end | 0 | 2 | 17 | 0 | 0 | 0 | 0 | 0 |
| | | | 0 | 0 | 0 | 0 | 0 | 0 | 0 | 0 |
| CH | 18–20 | As above. Sample A/W in both directions from control head, sample $CO_2$ from control head to light guide as well as entire channel | 0 | P24[g] E 9 | 41[h] | 0 | 0 | 0 | 0 | 0 |
| | | | 0 | P6 E17 | 16[i] | 0 | 0 | 0 | 0 | 0 |
| CH | 18–20 | Clamp on $CO_2$ valve to hold it open, smaller restrictor on A/W connector on light guide end | 0 | 2 | 6 | 0 | 0 | 0 | 0 | 0 |
| | | | 0 | 0 | 0 | 0 | 0 | 0 | 0 | 0 |
| | | | 0 | 0 | 1 | 0 | 0 | 0 | 0 | 0 |
| LG | 18–20 | Connect suction & A/W only, tight | 0 | 0 | 0 | 0 | 0 | 0 | 0 | 0 |
| | | | 0 | 1 | 0 | 0 | 0 | 0 | 0 | 0 |

TABLE II-continued

DETAILED DATA TABLE:
Improved Application of Liquids to Lumens by Reverse Flow
Sterilization of endoscopes on an automatic endoscope
reprocessor, 40–45° C, 15% performic acid based
sterilant in RO water, 10-minute exposure.

|  |  |  | Number of survivors[k] | | | | | | | |
|---|---|---|---|---|---|---|---|---|---|---|
| Conn[f] | Chann press | Other | Suct[a] | $CO_2$[b] | ACP[j] | Ext | A/W port | $CO_2$ valve | Suct Port | A/W port LG |
| LG |  | restrictor on prong, standard inoculum | | | | | | | | |
| LG |  | Connect suction, A/W, and $CO_2$, no restrictor, standard inoculum, run at 400 rpm as has been done above to reduce foam | 0<br>5 | 2<br>0 | 2<br>1 | 0<br>0 | 0<br>0 | 0<br>0 | 0<br>0 | 0<br>0 |
| LG | 9–10 | Connect suction, A/W and $CO_2$, no restrictor, standard inoculum, run at 800 rpm, foamy | 0<br>0<br>0 | 0<br>1<br>0 | 1<br>0<br>4 | 0<br>0<br>0 | 0<br>0<br>0 | 0<br>0<br>0 | 0<br>0<br>0 | 0<br>0<br>0 |
| LG | 9–10 | As above except try to inoculate distal end only of air/water/$CO_2$ channel (~0.3 ml inoculum rather than 5) | 0<br>0 | 0<br>2 | 0<br>2 | 0<br>0 | 0<br>0 | 0<br>0 | 0<br>0 | 0<br>0 |
| LG | 9–10 | As above except lay scopes as flat as possible in rear of bay | 0<br>0 | 1<br>5 | 0<br>A/W = 3[j]<br>6<br>A/W = 2 | 0<br>0 | 0<br>0 | 0<br>0 | 0<br>0 | 0<br>0 |
| LG | 13–14 | Connect suction, A/W and air prong, standard inoculum, 800 rpm | 0<br>0<br>0<br>0 | 0<br>0<br>17<br>2 | 0<br>0<br>33<br>A/W = 4<br>2 | 0<br>Mold<br>0<br>0 | 0<br>0<br>0<br>0 | 0<br>0<br>0<br>0 | 0<br>0<br>0<br>0 | 0<br>0<br>0<br>0 |
|  | 10–12 | Connect suction, A/W, restrictor on prong. Inoculate exterior- back of knob, insertion tube, control head | 0<br>0 | 0<br>28 | 0<br>14<br>A/W = 1 | 0<br>0 | 0<br>0 | 0<br>0 | 0<br>0 | 0<br>0 |
|  | 11–12 | Purge with air for 5 sec in every minute of exposure, connect as above | 0<br>0 | 6<br>4 | 1<br>A/W = 1<br>1 | 0<br>0 | 0<br>0 | 0<br>0 | 0<br>0 | 0<br>0 |
|  | 12–13 | Purge with air for 15 sec every other minute of exposure (total of 4 times), connect as above | 0 | 1 | 3 | 0 | 0 | 0 | 0 | 0 |

TABLE II-continued

DETAILED DATA TABLE:
Improved Application of Liquids to Lumens by Reverse Flow
Sterilization of endoscopes on an automatic endoscope
reprocessor, 40–45° C, 15% performic acid based
sterilant in RO water, 10-minute exposure.

| | | | Number of survivors[k] | | | | | | | |
|---|---|---|---|---|---|---|---|---|---|---|
| Conn[f] | Chann press | Other | Suct[a] | $CO_2$[b] | ACI[j] | Ext | A/W port | $CO_2$ valve | Suct Port | A/W port LG |
| | 10–13 | Alternate | 0 | 0 | 0 | 0 | 0 | 0 | 0 | 0 |
| | | direction | 0 | 0 | 0 | 0 | 0 | 0 | 0 | 0 |
| | | of flow in | 0 | 0 | 0 | 0 | 0 | 0 | 0 | 0 |
| | | $CO_2$ channel | 0 | 0 | 0 | 0 | 0 | 0 | 0 | 0 |
| | | every | 0 | 0 | 0 | 0 | 0 | 0 | 0 | 0 |
| | | minute of | 0 | 0 | 0 | 0 | 0 | 0 | 0 | 0 |
| | | exposure, | 0 | 0 | 0 | 0 | 0 | 0 | 0 | 0 |
| | | | 0 | 0 | 0 | 0 | 0 | 0 | 0 | 0 |
| | | | 0 | 0 | 0 | 0 | 0 | 0 | 0 | 0 |
| | | No preheat, otherwise as above | 0 | 0 | 0 | 0 | 0 | 0 | 0 | 0 |

[a]Suction channel flushed and brushed first
[b]$CO_2$ channel flushed with syringe then all channels flushed with all-channel irrigator for ACI count
[c]The tubing connection to the air/water and $CO_2$ channels was disconnected when the scope was partially removed from the chamber. It is possible that it came loose during the cycle.
[d]The exposure cycle was stopped for about 1 minute. The light guide end fell off the rack and pulled a tubing connection loose.
[e]Filters clogged during survivor recovery from neutralizer, most probably due to agar present in the neutralizer from previous use of bottle
[f]LG = light guide, CH = control head
[g]P = control head to light guide, E = entire length of channel
[h]A/W only -- proximal (CH to LG) = 0, distal end (CH to nozzle) = 3
[i]A/W proximal = 0, distal end = 0
[j]After (and including) 46th test sampled the air and water channels from the light guide end to distal tip. This was done after the gas channel sampling but before the ACI. Results are reported only if there were survivors.
[k]If the number of survivors is >0, the test failed.

Although the description of the preferred embodiment has been presented, it is contemplated that various changes, including those mentioned above, could be made without deviating from the spirit of the present invention. It is therefore desired that the present embodiment be considered in all respects as illustrative, not restrictive, and that reference be made to the appended claims rather than to the foregoing description to indicate the scope of the invention.

I claim:

1. A method of sterilizing a tubular structure comprising:
   a) providing a tubular structure having first and second flow paths defined therethrough;
   b) providing at least one source of sterilizing fluid;
   c) selectively communicating a proximal end of said first fluid flow path with said at least one source of sterilizing fluid;
   d) causing said sterilizing fluid to flow at a positive pressure through said tubular structure along said first fluid flow path;
   e) selectively communicating a proximal end of said second fluid flow path with said at least one source of sterilizing fluid; and
   f) causing said sterilizing fluid to reverse flow at a positive pressure through said tubular structure along said second fluid flow path, wherein at least part of said second fluid flow path is opposite said first fluid flow path.

2. The method of claim 1 wherein said sterilizing fluid is below about 50 degrees C. and said sterilizing fluid is provided from about 1 minute to about 20 minutes.

3. The method of claim 1 wherein said tubular structure has a diameter of less than about 6 mm and wherein said flow and said reverse flow are from about 50 cm/second to about 500 cm/second and below about 20 psi.

4. The method of claim 1 wherein said flow and said reverse flow are from about 100 ml/min to about 1400 ml/min and below about 20 psi.

5. The method of claim 1 wherein said tubular structure is a lumen of a medical device.

6. The method of claim 5 wherein one of said fluid flow paths starts in a control head of said medical device.

7. The method of claim 5 wherein said first fluid flow path and said second fluid flow path start in one end of said medical device.

8. The method of claim 1 further comprising providing a device including:
   a) a first valve and a second valve;
   b) said first and second valves in fluid communication with said at least one source of sterilizing fluid, said fluid being maintained at a positive pressure;
   c) said first valve in fluid communication with said proximal end of said first fluid flow path;
   d) said second valve in fluid communication with said proximal end of said second fluid flow path;
   e) the first fluid flow path being in fluid communication with the second fluid flow path;
   f) said first and second valves selectively switchable between a first position and a second position;
   g) wherein in said first position said first valve is open to the fluid supply and said second valve is closed to the fluid supply, and
   h) wherein in said second position said second valve is open to the fluid supply and said first valve is closed to the fluid supply.

9. The method of claim 1 wherein said flow and said reverse flow are controlled by a central processor.

10. The method of claim 1 wherein said tubular structure is long and narrow.

11. The method of claim 1 wherein said tubular structure has a length and a diameter, said length from about 200 to about 8000 times said diameter.

12. The method of claim 1 wherein said sterilizing fluid is a liquid.

13. The method of claim 1, wherein said selectively communicating a proximal end of said first flow path comprises operating a valve provided at said proximal end of said first flow path to communicate said first flow path with said source of sterilizing fluid.

14. The method of claim 13, wherein said step of selectively communicating a proximal end of said second flow path comprises operating a second valve provided at said proximal end of said second flow path to communicate said second flow path with said source of sterilizing fluid.

15. The method of claim 1, further comprising during e), communicating said first flow path proximal end to drain.

16. The method of claim 1, further comprising during c), communicating said second flow path proximal end to drain.

17. The method of claim 14 wherein said first fluid flow path is downstream except for upstream through a control air channel, upstream through an air/water cylinder, upstream through an umbilical air channel, upstream through an air/water supply port, upstream through said second valve, and upstream through an umbilical water channel; and said second fluid flow path is downstream except for upstream through a control $CO_2$ channel, upstream through a $CO_2$ cylinder, upstream through an umbilical $CO_2$ channel, upstream through a $CO_2$ supply port, and upstream through said first valve.

* * * * *

UNITED STATES PATENT AND TRADEMARK OFFICE
CERTIFICATE OF CORRECTION

PATENT NO. : 6,797,234 B2
DATED : September 28, 2004
INVENTOR(S) : Patricia M. Stanley It is certified that error appears in the above-identified patent and that said Letters Patent is hereby corrected as shown below:

Column 12,
Line 35, delete "proofmg" and substitute -- proofing -- therefor.

Column 16,
Line 13, delete "flow lo through" and substitute -- flow through -- therefor.

Signed and Sealed this

Twenty-sixth Day of July, 2005

JON W. DUDAS
*Director of the United States Patent and Trademark Office*